(12) United States Patent
Lutsen et al.

(10) Patent No.: US 8,450,604 B2
(45) Date of Patent: May 28, 2013

(54) POLYMERISABLE COMPOUNDS FOR MAKING OPTO-ELECTRONIC DEVICES

(75) Inventors: Laurence Lutsen, Coudekerque-Branche (FR); Dirk Vanderzande, Hasselt (BE); Bert Campo, Bouwel (BE)

(73) Assignees: IMEC, Leuven (BE); Universiteit Hasselt, Diepenbeek (BE)

( * ) Notice: Subject to any disclaimer, the term of this patent is extended or adjusted under 35 U.S.C. 154(b) by 211 days.

(21) Appl. No.: 13/001,603

(22) PCT Filed: Apr. 3, 2009

(86) PCT No.: PCT/EP2009/054056
§ 371 (c)(1),
(2), (4) Date: Feb. 2, 2011

(87) PCT Pub. No.: WO2010/000504
PCT Pub. Date: Jan. 7, 2010

(65) Prior Publication Data
US 2011/0130522 A1    Jun. 2, 2011

Related U.S. Application Data

(60) Provisional application No. 61/077,024, filed on Jun. 30, 2008.

(30) Foreign Application Priority Data

Jun. 30, 2008 (GB) .................................. 0811930.7

(51) Int. Cl.
*H01L 31/00* (2006.01)
(52) U.S. Cl.
USPC ....................................................... 136/263
(58) Field of Classification Search
USPC ................... 136/263; 525/535, 451; 528/377, 528/378, 380
See application file for complete search history.

(56) References Cited

U.S. PATENT DOCUMENTS

| 3,097,230 A | 7/1963 | Miller |
| 2007/0290194 A1 | 12/2007 | Becker et al. |
| 2007/0295389 A1* | 12/2007 | Capps et al. ................. 136/251 |

FOREIGN PATENT DOCUMENTS

| JP | 63 077872 A | 4/1988 |
| JP | 2008 047855 A | 2/2008 |
| WO | WO 2008/001051 A2 | 1/2008 |
| WO | WO 2008/053158 A | 5/2008 |

OTHER PUBLICATIONS

Lowe, J., et al.; Macromolecules, 1995, p. 4608-4616.*
Miller, J.S.; Advanced Materials, 1993, p. 587-589.*
Matsuda Thtsuhito et al., "Novel thiophene methacrylates for materials of high refractive index", Journal of Macromolecular Science: Part A—Chemistry, Marcel Dekker, New York, NY, US, vol. A36, No. 9, Aug. 1, 1999, pp. 1271-1288.
Database WPI, Week 1988, Thompson Scientific, London, GB; AN 1988-136356, XP002538792 New (di)bromo-2-methacrylic:oxy:methyl:thiophene(s)—use ful as optical plastics., prepd. e.g. by reaction of brominated 2-halo:methyl:thiophene with methacrylic acid salts.
Sybille Allard et al. "Oligothiophenes for pattern formation by stamping", Macromol. Chem. Phys., vol. 204, No. 1, 2003, pp. 68-75.
Z. Zhu et al., "Stabilization of Flim Morphology in Polymer-Fullerene Heterojunction Solar Cells", Journal of Macromolecular Science; Part A—Pure and Applied Chemistry, vol. 41, No. 12, 2004, pp. 1467-1487.

* cited by examiner

*Primary Examiner* — Robert Jones, Jr.
(74) *Attorney, Agent, or Firm* — Knobbe Martens Olson & Bear, LLP

(57) ABSTRACT

This invention provides monomeric compounds represented by the structural formula (I) or the structural formula (II) which can be polymerized into crosslinkable polymers useful for producing opto-electronic devices.

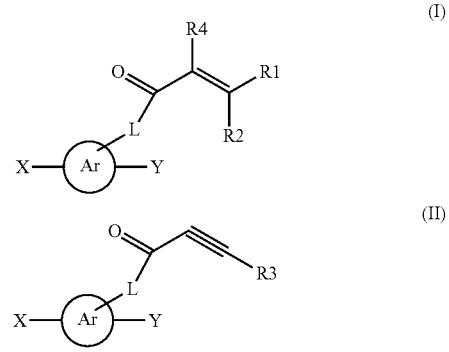

14 Claims, 18 Drawing Sheets

POLYMERISABLE COMPOUNDS FOR MAKING OPTO-ELECTRONIC DEVICES

CROSS-REFERENCE TO RELATED APPLICATIONS

This application is the national phase under 35 U.S.C. §371 of prior PCT International Application No. PCT/EP2009/054056, which has an International Filing Date of Apr. 3, 2009, which designates the United States of America, and which claims priority to U.S. Provisional Application No. 61/077,024, filed on Jun. 30, 2008, and Great Britain Application No. GB 0811930.7, filed on Jun. 30, 2008, the disclosures of which are hereby expressly incorporated by reference in their entirety and are hereby expressly made a portion of this application.

FIELD OF THE INVENTION

The present invention relates to aromatic polymerisable compounds, as well as conjugated polymers made therefrom having either p-type or n-type properties, blends of such polymers with n-type or p-type compounds respectively, and opto-electronic devices made by cross-linking such blends preferably in the absence of a photoinitiator. The present invention also relates to methods for producing and polymerising such aromatic polymerisable compounds, and methods for crosslinking blends of such polymers and n-type or p-type compounds.

BACKGROUND OF THE INVENTION

Photosensitive polymers with photo-crosslinkable groups have gained a considerable interest in recent years owing to a wide variety of applications in the field of photoresist, photocurable coatings, microlithography, etc.

Also in the field of organic semi-conducting materials, the interest in crosslinkable materials is increasing, notably for electroluminescent devices and the application of the active layer in a direct structured manner, avoiding then the use of shadow masks.

An approach has been proposed in U.S. Pat. 2007/0290194 in which a crosslinking process using oxetane-functionalized organic semiconductors and conductors is proposed. In this procedure the crosslinking reaction is initiated by UV irradiation in the presence of at least one added onium compound as photoinitiator.

Another approach has been proposed in WO 2008/001051A2 wherein the active layer of the organic based device (mainly OLED, PLED, organic capacities touch sensor and bi-layer photovoltaics) is a semi-conducting polymer made from a polymerisable ink formulation comprising a liquid formed from a UV reactive resin monomer (monomer), a UV reactive thinner (oligomer) and a photoinitiator: the ink is configured for polymerization by UV exposure into a (semi-conducting) polymer film.

However the disadvantage of an admixed electronically active compound such as a photoinitiator is that it cannot be removed from the film after crosslinking and therefore can act as an impurity, adversely affecting the film composition, the film morphology and then affecting the functioning of the organic device. This is even more true for organic devices such as organic bulk hetero-junction solar cells in which the nano-morphology of the active layer is very sensitive to any parameter change (during the fabrication process but also during time after fabrication) and then to the power efficiency of the cell.

Other methods towards crosslinkable semi-conducting polymers, mainly polythiophenes, have been reported in which no photoinitiator is used, but they show many drawbacks:

G. Zotti in *Synthetic Metals* (1999) 105:135 has polymerized by electrochemistry an acrylated monomer giving a totally insoluble polymer;

B. de Ruiter in *Synthetic Metals*, (1996) 79:215-218 has polymerized by oxidative polymerization an acrylated monomer but this method shows interference between the acrylate chemistry and the radical chain process leading to a very difficult control of the polymer fabrication (e.g. linear polymer chain are difficult to reach, with high polydispersity values even for very short reaction times).

Zhu et al. in *Journal of Macromolecular Science* (2004) 41:1467-1487 reports the synthesis of epoxy-functionalized polythiophene derivatives. A slow degradation of cells made from poly(3-hexylthiophene) and a fullerene derivative of butyric acid methyl ester was observed due to a change of phase morphology.

SUMMARY OF THE INVENTION

It is an object of the present invention to provide new crosslinkable semi-conductive materials suitable for use in opto-electronic devices as well as opto-electronic devices comprising such materials.

It is an advantage of some embodiments of the present invention that crosslinkable semi-conducting materials can be produced that permit to stabilise in time the nano-morphology of an active layer comprising said crosslinkable semi-conducting materials. For instance, an active layer in organic bulk heterojunction solar cells comprising a semi-conducting material according to an embodiment of the present invention can have its nano-morphology stabilised upon cross-linking of said material.

It is another advantage of some embodiments of the present invention that the stabilisation of the morphology is accompanied by a stabilisation of the performances of the device, such as for instance the stabilisation of the power efficiency and/or the short circuit current of a bulk heterojunction solar cell.

It is another advantage of some embodiments of the present invention that the stabilisation of the morphology is accompanied by an increase in the lifetime to predetermined performance levels of the devices, in particular solar cells.

It is another advantage of some embodiments of the present invention that the stability in time of the power efficiency of the solar cells may be linked to the stability in time of the active layer. This active layer may be processed as a thin film from an organic solvent in which both p- and n-type components are soluble, and may be made from a blend of a p-type semi-conducting polymer and a n-type material (for example a C60 fullerene derivative or a n-type semi-conducting polymer) which would tend to de-mix with time if not properly stabilised according to the teachings of this invention.

It is an object of the present invention to provide a stable active layer based on a blend of p-type and n-type materials for bulk heterojunction solar cell applications. This blend may be made of a p-type semi-conducting material containing specific crosslinkable functions as side chains and a n-type material mixed together in various ratios and processed e.g. as a thin film from solution. The n-type material included in such blends can be any previously known small molecule, oligomer or polymer optionally containing known crosslinkable functions as side chains.

In a first aspect, the present invention provides a class of monomeric compounds represented by the structural formula (I)

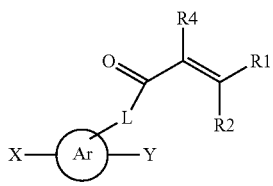

and a class of monomeric compounds represented by the structural formula (II)

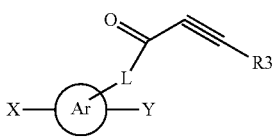

wherein:
Ar is a homocyclic or heterocyclic aromatic group selected from the group consisting of thienyl, phenyl, naphthyl, pyrrolyl, pyridyl, carbazolyl, fluorenyl and benzothiazolyl;
L is selected from the group consisting of —O—, —CH$(CH_3)$—O—, —$(CH_2)_q$—O—, —NH—, —CH$(CH_3)$—NH—, —$(CH_2)_q$—NH—, —S—, —CH$(CH_3)$—S— and —$(CH_2)_q$—S—, the oxygen atom of said —CH$(CH_3)$—O— or —$(CH_2)_q$—O—, being adjacent to the carbonyl group, the NH group of said —CH$(CH_3)$—NH— or —$(CH_2)_q$—NH—, being adjacent to the carbonyl group and the sulphur atom of said —CH$(CH_3)$—S— or —$(CH_2)_q$—S—, being adjacent to the carbonyl group;
q is 1, 2, 3, 4, 5, 6, 7, 8, 9, 10, 11 or 12;
$R_1$ and $R_2$ are independently selected from the group consisting of hydrogen, $C_{1-12}$ alkyl and phenyl, wherein said phenyl is optionally substituted with one or more substituents independently selected from the group consisting of hydroxyl, halogen, metonym, $C_{2-4}$-alkoxy and trifluoromethyl;
$R_3$ is selected from the group consisting of hydrogen, $C_{1-12}$-alkyl and phenyl;
$R_4$ is hydrogen, methyl or $C_{2-4}$-alkyl; and
X and Y are independently selected from the group consisting of hydrogen, chloro, bromo, iodo, boronic acid, boronic esters and organotin, provided that X and Y are not both hydrogen. In a preferred embodiment of the first aspect L is selected from the group consisting of —O—, —CH$(CH_3)$—O—, —$(CH_2)_q$—O—, —NH— or —S—, the oxygen atom of said —CH$(CH_3)$—O— or —$(CH_2)_q$—O—, being adjacent to the carbonyl group.

In a second aspect, the present invention provides conjugated polymers comprising one or more repeating units derived from the above-defined monomeric compounds represented by the structural formula (I) or the structural formula (II), and optionally one or more repeating units derived from a co-monomer copolymerisable with said monomeric compound, the latter repeating units comprising a divalent homocyclic or heterocyclic aromatic group Ar' optionally substituted with one or more substituents independently selected from the group consisting of $C_{1-20}$-alkyl, $C_{1-20}$-alkoxy, $C_{1-20}$-alkylsulfate, phenyl, benzyl, and functional crosslinkable groups.

In a third aspect, the present invention provides methods for producing an above-defined monomeric compounds represented by the structural formula (I) or the structural formula (II), comprising reacting a hydroxyl-substituted homocyclic or heterocyclic aromatic compound represented by the structural formula (III)

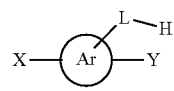

wherein Ar, X, Y and L are as defined above, with an ethylenically unsaturated carbonyl chloride represented by the structural formula (IV)

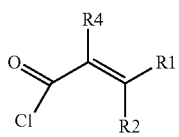

wherein $R_1$, $R_2$ and $R_4$ are as defined above, or the corresponding carboxylic anhydride,
or with an acetylenically unsaturated carbonyl chloride represented by the structural formula (V)

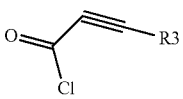

wherein $R_3$ is as defined above.

In a fourth aspect, the present invention provides a method for producing the above-described polymer comprising polymerising a compound represented for formula (I) or formula (II) by reductive coupling.

In a fifth aspect, the present invention provides a method for producing the above-described polymer comprising copolymerising by reductive coupling a compound according to formula (I) or formula (II) and one or more co-monomers.

In a sixth aspect, the present invention provides a process for preparing a polymer comprising the following steps: copolymerization of a monomer post-functionalisable to a compound represented by structural formula (I) or structural formula (II) as defined above with a co-monomer copolymerisable therewith, said co-monomer being a divalent homocyclic or heterocyclic aromatic group Ar' optionally substituted with one or more substituents independently selected from the group consisting of $C_{1-20}$-alkyl, $C_{1-20}$-alkoxy, $C_{1-20}$-alkylsulfate, phenyl and benzyl, to produce a post-functionalisable copolymer; and post-functionalizing said post-functionalisable copolymer to produce the polymer of the fifth aspect. Examples of monomers post-functionalisable to a compound represented by structural formula (I) are esters of 3-(2-hydroxyethyl)thiophene e.g. 3-(2-acetoxyethyl) thiophene.

In a seventh aspect, the present invention provides blends of a n-type or p-type compound and a conjugated polymer or conjugated copolymer derived from a monomeric compound represented by the structural formula (I) or the structural formula (II).

In an eighth aspect, the present invention provides crosslinked polymer materials, and methods for producing the same, being irradiated, e.g. UV-irradiated, blends as mentioned before preferably in the absence of a photoinitiator.

In yet another aspect, the present invention provides optoelectronic devices such as, but not limited to, solar cells comprising a crosslinked polymer material as defined above, i.e. obtained from irradiated blends of a n-type or p-type compound and a conjugated polymer or copolymer derived from an above-defined monomeric compound.

DEFINITIONS

Figure 1:
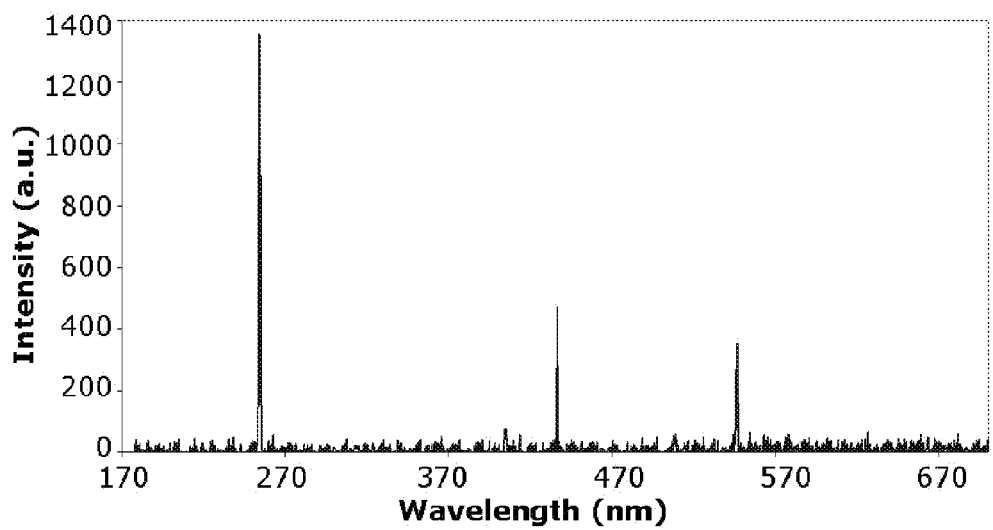
FIG. 1 shows the UV spectrum of an irradiation lamp used to operate cross-linking in an embodiment of the present invention.

As used herein with respect to a substituting group, and unless otherwise stated, the term "$C_{1-12}$ alkyl" refers to a straight (non-branched) or branched chain saturated acyclic hydrocarbon monovalent group having from 1 to 4 carbon atoms such as, for example, methyl, ethyl, propyl, n-butyl, 1-methyl-ethyl(isopropyl), 2-methylpropyl(isobutyl), and 1,1-dimethylethyl(tert-butyl). Similarly, the term "$C_{1-20}$ alkyl" refers to straight (non-branched) or branched chain groups having from 1 to 20 carbon atoms such as, for example, pentyl, hexyl, heptyl, octyl, nonyl, decyl, dodecyl, tetradecyl, hexadecyl, octadecyl and the like.

As used herein with respect to a substituting group, and unless otherwise stated, the terms "homocyclic aromatic" or "aryl" designate any mono- or polycyclic aromatic monovalent hydrocarbon group having from 6 to 15 carbon atoms such as, but not limited to, phenyl, naphthyl, anthracenyl, phenanthracyl, fluoranthenyl, chrysenyl, pyrenyl, biphenylyl, terphenyl, picenyl, indenyl, biphenyl, indacenyl, tetrahydropyrenyl, benzocyclobutenyl, benzocyclooctenyl and the like, including fused benzo-$C_{4-8}$ cycloalkyl groups such as, for instance, indanyl, tetrahydronaphthyl, fluorenyl and the like, all of the said groups being optionally substituted with one or more substituents (preferably 1 to 3 substituents) independently selected from the group consisting of halogen, $C_{1-12}$ alkyl, nitro, trifluoromethoxy, trifluoromethyl and $C_{1-12}$ alkoxy (all of such substituents being such as herein defined, including individual species and sub-groups thereof), such as, but not limited to, 4-fluorophenyl, 4-chlorophenyl, 3,4-dichlorophenyl, 2,6-dichlorophenyl, 2-fluorophenyl, 3-chlorophenyl, 3,5-dichlorophenyl, trifluoromethylphenyl, 3,4-dimethoxyphenyl, iodophenyl, and bromophenyl.

As used herein with respect to a substituting group, and unless otherwise stated, the terms "heterocyclic aromatic" or "heteroaryl" means a mono- or polycyclic, polyunsaturated, monovalent hydrocarbon group having from 4 to 12 carbon atoms and including one or more heteroatoms in one or more heterocyclic rings, each of said rings having 5 or 6 atoms (and optionally further including one or more heteroatoms attached to one or more carbon atoms of said ring, for instance in the form of a carbonyl, and/or to one or more heteroatoms of said ring, for instance in the form of a N-oxide), each of said heteroatoms being independently nitrogen or sulfur, also including groups wherein a heterocyclic ring is fused to one or more aromatic homocyclic rings for instance in the form of benzo-fused, dibenzo-fused and naphtho-fused heterocyclic groups; within this definition are included heteroaryl groups such as, but not limited to, thienyl, pyrrolyl, pyridyl, carbazolyl and benzothiazolyl.

As used herein with respect to a substituting atom, and unless otherwise stated, the term "halogen" means any atom selected from the group consisting of fluorine, chlorine, bromine and iodine.

As used herein with respect to a substituting group, and unless otherwise stated, the term "$C_{1-12}$ alkoxy" refers to substituents wherein a carbon atom of a $C_{1-20}$ alkyl group (such as defined herein above, including sub-groups thereof), is attached to an oxygen atom through a single bond, including methoxy, ethoxy, propoxy, n-butoxy, isopropoxy, sec-butoxy, and tert-butoxy.

As used herein with respect to a substituting group, and unless otherwise stated, the term "$C_{1-20}$ alkylsulfate" refers to substituents wherein a carbon atom of a $C_{1-20}$ alkyl group (such as defined herein above, including sub-groups thereof), is attached to an oxygen atom of a sulfate group through a single bond such as, but not limited to methylsulfate (methoxysulfonyloxy), ethylsulfate (ethoxysulfonyloxy), n-butylsulfate (n-butoxysulfonyloxy), tea-butylsulfate (tert-butoxysulfonyloxy), undecylsulfate (undecyloxysulfonyloxy), and the like.

As used herein, and unless otherwise stated, the term "arylene" designates any divalent group derived from aryl (such as above defined) by abstracting a hydrogen atom.

As used herein, and unless otherwise stated, the term "heteroarylene" designates any divalent group derived from heteroaryl (such as above defined) by abstracting a hydrogen atom.

As used herein, and unless otherwise stated, "crosslinkable" refers to the capacity of being irreversibly cured or polymerized, thereby forming a material that cannot be reshaped or reformed.

As used herein with respect to a substituting group, and unless otherwise stated, the term "functional crosslinkable" group designates moieties containing one or more functionalities selected from the group consisting of double bond, triple bond, or precursors thereof, or addition-polymerisable groups known in the art. Suitable crosslinkable groups include vinyl, allyl, or may be derived from acrylates, methacrylates, vinyl ethers, 1-propenyl ethers, arylene containing one or more substituents independently selected from the group consisting of benzocyclobutane, azide, di(hydrocarbyl)amino, cyanate, ester, hydroxyl, glycidyl ether, $C_{1-20}$ alkyl acrylates, $C_{1-20}$ alkyl methacrylates, alkenyl, alkenyloxy, alkynyl, maleimide, vinylbenzyl, allyloxy, p-ethenylphenyl, perfluoroethenyl, perfluoroethenyloxy, coumaroyl, and halogenated derivatives thereof.

As used herein with respect to organic devices, and unless otherwise stated, the term "active layer" designates an organic layer which includes an organic semiconductor material exhibiting one type of electronic conductivity and possibly a second semiconductor material having the same or opposite type conductivity.

As used herein with respect to an active, and unless otherwise stated, the term "stable" refers to the adequate nanomorphology of the active layer which does not change in time at room temperature or even at higher temperature under inert atmosphere.

As used herein, and unless otherwise stated, the term "boronic ester" refers to a boronic acid derivative wherein hydrogen is replaced by any organic residue, preferably a hydrocarbyl group, and which can be obtained by condensation with alcohols or diols, including but not limited to dioxaborolanes and dioxaborinanes.

As used herein, and unless otherwise stated, the term "organotin" refers to a group represented by the structural formula $SnR_9R_{10}R_{11}$ wherein each of $R_9$, $R_{10}$ and $R_{11}$ is independently selected from the group consisting of halogen, $C_{1-20}$ alkyl, $C_{3-10}$ cycloalkyl, aryl, benzyl and $C_{2-7}$ alkenyl, provided that $R_9$, $R_{10}$ and $R_{11}$ are not simultaneously halogen; such organotin groups may be derived from tin compounds including, but not limited to, di-n-butyltin dibromide, di-n-butyltin dichloride, di-tert-butyltin dichloride, dimethyltin dibromide, dimethyltin dichloride, dimethyltin difluoride, dimethyltin diiodide, diphenyltin dichloride, diphenyltin dibromide, diphenyltin difluoride, diphenyltin diiodide, tributyltin fluoride, tributyltin chloride, tributyltin bromide, tributyltin iodide, phenyltin tribromide, phenyltin trichloride, tricyclohexyltin chloride, triethyltin bromide, triethyltin chloride, triethyltin iodide, vinyltributyltin, tetrabutyltin, butyltin trichloride, n-butylvinyltin dichloride, diallyldibutyltin, diallyldiphenyltin, dibutylvinyltin bromide, dibutylvinyltin chloride, dichlorodi-m-tolylstannane, diethyldiisoamyltin, diethyldiisobutyltin, diethyldiphenyltin, diethylisoamyltin bromide, diethylisoamyltin chloride, diethylisobutyltin bromide, diethyl-n-propyltin bromide, diethyl-n-propyltin chloride, diethyl-n-propyltin fluoride, diethyltin dibromide, diethyltin dichloride, diethyltin difluoride, diethyltin diiodide, diisoamyltin dibromide, diisoamyltin dichloride, diisoamyltin diiodide, diisobutyltin dichloride, diisobutyltin diiodide, diisopropyltin dichloride, diisopropyltin dibromide, dimethyldiethyltin, dimethyldiisobutyltin, dimethyldioctyltin, dimethyldivinyltin, dimethylethylpropyltin, dimethylethyltin iodide, dimethyldivinyltin, dimethylvinyltin bromide, dimethylvinyltin iodide, diphenyldivinyltin, dipropyltin difluoride, dipropyltin diiodide, dipropyltin dichloride, dipropyltin dibromide, di-o-tolyltin dichloride, di-p-tolyltin dichloride, ditriphenyl-stannylmethane, divinylbutyltin chloride, divinyltin dichloride, ethyldiisoamyltin bromide, ethyldiisobutyltin bromide, ethylmethylpropyltin iodide, ethyl-n-propyldiisoamyltin, ethylpropyltin dichloride, ethyltin tribromide, ethyltin triiodide, ethyltri-n-butyltin, ethyltri-n-propyltin, methyltin tribromide, methyltin trichloride, methyltin triiodide, methyltri-n-butyltin, methyltri-n-propyltin, phenylbenzyltin dichloride, phenyltribenzyltin, propyltin triiodide, propyltri-n-amyltin, tetra-n-amyltin, tetra-n-butyltin, tetrabenzyltin, tetracyclohexyltin, tetraethyltin, tetra-n-heptyltin, tetra-n-hexyltin, tetraisoamyltin, tetraisobutyltin, tetralauryltin, tetramethyltin, tetra-n-octyltin, tetraphenyltin, tetrapropyltin, tetra-o-tolyltin, tetra-m-tolyltin, tetra-p-tolyltin, tetravinyltin, tetra-m-xylyltin, tetra-p-xylyltin, o-tolyltin trichloride, p-tolyltin trichloride, m-tolyltrichlorostannane, triallylbutyltin, tri-n-amyltin bromide, tribenzylethyltin, tribenzyltin chloride, tribenzyltin iodide, tri-n-butyltin bromide, tri-n-butylvinyltin, triethyl-n-amyltin, triethylisoamyltin, triethylisobutyltin, triethylphenyltin, triethyl-n-propyltin, triisoamyltin bromide, triisoamyltin chloride, triisoamyltin fluoride, triisoamyltin iodide, triisobutylethyltin, triisobutylisoamyltin, triisobutyltin bromide, triisobutyltin chloride, triisobutyltin fluoride, triisobutyltin iodide, triisopropyltin bromide, triisopropyltin iodide, trimethyldecyltin, tri methyldodecyltin, trimethylethyltin, trimethyltin bromide, trimethyltin chloride, trimethyltin fluoride, trimethyltin iodide, triphenylallyltin, triphenylbenzyltin, triphenylbutyltin, triphenylethyltin, triphenylmethyltin, triphenyl-α-naphthyltin, triphenyltin bromide, triphenyltin chloride, triphenyltin fluoride, triphenyltin iodide, triphenyl-p-tolyltin, triphenyl-p-xylyltin, tri-n-propyl-n-butyltin, tri-n-propylethyltin, tri-n-propylisobutyl tin, tri-n-propyltin chloride, tri-n-propyltin fluoride, tri-n-propyltin iodide, tri-o-tolyltin bromide, tri-p-tolyltin bromide, tri-o-tolyltin chloride, tri-m-tolyltin chloride, tri-p-tolyltin chloride, tri-p-tolyltin fluoride, tri-o-tolyltin iodide, tri-p-tolyltin iodide, triphenylstannylmethane, trivinyldecyltin, trivinylhexyltin, trivinyloctyltin, trivinyltin chloride, vinyltin trichloride, tri-p-xylyltin bromide, tri-p-xylyltin chloride, tri-p-xylyltin fluoride, tri-p-xylyltin iodide and tri-m-xylyltin fluoride.

DETAILED DESCRIPTION OF THE INVENTION

Within the first aspect of this invention, as described in the Summary of the Invention, the following more specific embodiments are of particular importance:

compounds represented by the structural formula (I) or the structural formula (II) wherein L is adjacent to X or Y;

compounds represented by the structural formula (I) wherein $R_1$ and $R_2$ are both hydrogen, and $R_4$ is methyl, which may be derived from methacryloyl chloride, as explained below with regard to the third aspect of the invention;

compounds represented by the structural formula (I) wherein $R_1$ and $R_4$ are hydrogen, and wherein $R_2$ is methyl or ethyl or n-propyl or n-butyl, or $R_2$ is phenyl optionally mono-substituted with fluoro, chloro, hydroxyl, methoxy, trifluoromethyl or $C_{2-4}$-alkoxy; such compounds may be derived from crotonyl chloride, pent-2-enoyl chloride, hex-2-enoyl chloride, hept-2-enoyl chloride, phenylprop-2-enoyl chloride, cinnamoyl chloride, 2-chlorocinnamoyl chloride, 4-fluorocinnamoyl chloride, 4-methoxycinnamoyl chloride, or analogs thereof as explained below with regard to the third aspect of the invention;

compounds represented by the structural formula (I) wherein $R_1$, $R_2$ and $R_4$ are hydrogen, which may be derived from acryloyl chloride, as explained below with regard to the third aspect of the invention; and compounds represented by the structural formula (II) wherein $R_3$ is hydrogen, methyl, ethyl, n-propyl or phenyl, which may be derived from propiolic acid chloride and analogs thereof, as explained below with regard to the third aspect of the invention.

Within the second aspect of this invention, as described in the Summary of the Invention, a more specific embodiment of particular importance consists of functionalized semi-conducting materials (conjugated materials), being oligomers, polymers or copolymers, containing one or more monomeric groups or repeating units represented by the structural formula (IA):

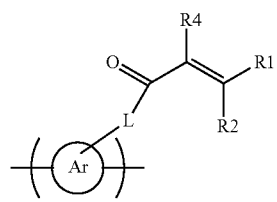

and/or represented by the structural formula (IIA):

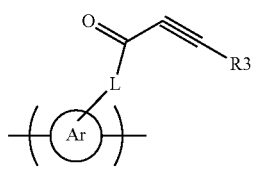

wherein Ar, L, $R_1$, $R_2$, $R_3$ and $R_4$ are as defined with respect to structural formulae (I) and (II), and optionally one or more monomeric groups or repeating units comprising a divalent group Ar' wherein Ar' may be arylene or heteroarylene, said Ar' being optionally substituted with one or more substituents independently selected from the group consisting of $C_{1-20}$-alkyl, $C_{1-20}$-alkoxy, $C_{1-20}$-alkylsulfate, aryl, benzyl, and functional crosslinkable groups known in the art.

More specifically Ar' may be 2,5-thienylene optionally substituted with one or more substituents independently selected from the group consisting of $C_{1-20}$-alkyl, $C_{1-20}$-alkoxy, $C_{1-20}$-alkylsulfate, phenyl, benzyl, and functional crosslinkable groups known in the art, e.g. 3-n-hexyl-2,5-thienylene or 3-n-octyl-2,5-thienylene.

The aromatic homocyclic or heterocyclic group Ar and the optionally substituted arylene or heteroarylene divalent group Ar' may be the same, e.g. they may be both 2,5-thienylene, or may be different.

In one embodiment, when said semi-conducting conjugated material is a copolymer containing one or more monomeric groups or repeating units represented by the structural formula (IA), wherein Ar is thienyl, and one or more monomeric groups or repeating units comprising a divalent group Ar' wherein Ar' is 3-$C_{1-20}$-alkyl-2,5-thienylene, then $R_1$ and $R_2$ are not both hydrogen.

In another embodiment, when said semi-conducting conjugated material is a copolymer containing one or more monomeric groups or repeating units represented by the structural formula (IA), wherein Ar is fluorenyl, and one or more monomeric groups or repeating units comprising a divalent group Ar' wherein Ar' is 2,7-fluorenylene, then $R_1$ and $R_2$ are not both hydrogen.

In another embodiment, the weight average molecular weight Mw (measured against a polystyrene standard) of the polymer or copolymer of this invention may be in the range from about 10,000 to about 1,000,000 Dalton, e.g. from about 40,000 to 75,000 Dalton;

In another embodiment, the polydispersity index (PD=Mw/Mn) of the polymer or copolymer of this invention may be comprised between 1.05 and about 5.0, e.g. between 1.1 and 3.0, or between about 1.3 and 2.5.

In a particular embodiment of this second aspect of the invention, the arylene or heteroarylene divalent group Ar' present in the recurring units of the co-monomer may be selected from the group consisting of 1,4-phenylene; 2,6-naphthalenediyl; 1,4-naphthalenediyl; 1,4-anthracenediyl; 2,6-anthracenediyl; 9,10-anthracenediyl; 2,5-thienylene; 2,5-furanediyl; 2,5-pyrrolediyl; 1,3,4-oxa-diazole-2,5-dyil; 1,3,4-thiadiazole-2,5-diyl; 2,3-benzo[c]thienylene; thieno[3,2-b]thiophene-2,5-diyl; pyrrolo[3,2-b]pyrrole-2,5-diyl; pyrene-2,7-diyl; 4,5,9,10-tetrahydropyrene-2,7-diyl; 4,4'-biphenylene; phenanthrene-2,7-diyl; 9,10-dihydrophenantrene-2,7-diyl; dibenzo-furane-2,7-diyl; dibenzothiophene-2,7-diyl; 2,5-selenophenylene; isothianaphthylene; 2,7-silafluorenylene; 3,6-carbazolediyl; pyridinediyl; 2,2'-dipyridinediyl; pyridopyrazinediyl; quinoxaline-diyl; thieno[3,4-c]pyridinediyl; thieno[3,4-b]pyridinediyl; thieno[3,4-b]pyrazine-diyl; benzothiadiazolediyl; 4H-cyclopenta[2,1-b; 3,4-b']dithienylene; silacyclo-pentadienediyl; and anthrazolinediyl. More specific examples of suitable co-monomers of this type are given below, together with literature references relating to their polymerisation techniques.

In a particular embodiment of this second aspect of the invention, the co-monomer comprising a divalent group Ar' may represent at least 0.5% by mole of the copolymer, e.g. at least 50% by mole of the copolymer, or at least 85% by mole of the copolymer. In another particular embodiment of this second aspect of the invention, the co-monomer comprising a divalent group Ar' may represent at most 99.5% by mole of the copolymer, e.g. at most 98% by mole of the copolymer, or at most 15% by mole of the copolymer.

Within the third aspect of this invention, as described in the Summary of the Invention, the following more specific embodiments are of particular importance:

the ethylenically unsaturated carbonyl chloride represented by the structural formula (IV) may be selected from the group consisting of crotonyl chloride, acryloyl chloride, methacryloyl chloride, pent-2-enoyl chloride, hex-2-enoyl chloride, hept-2-enoyl chloride, cinnamoyl chloride, 2-chlorocinnamoyl chloride, 4-fluorocinnamoyl chloride, and 4-methoxycinnamoyl chloride;

the acetylenically unsaturated carbonyl chloride represented by the structural formula (V) may be selected from the group consisting of propiolic acid chloride, phenylpropiolic acid chloride, 2-butynoic acid chloride, 2-pentynoic acid chloride, and 2-hexynoic acid chloride;

the hydroxyl-substituted homocyclic or heterocyclic aromatic compound represented by the structural formula (III) may be selected from the group consisting of 2,5-dibromo-3-hydroxyethyl thiophene, 2,5-dibromo-3-hydroxymethyl thiophene, 2,5-dibromophenol, 2-bromophenol, 3-bromophenol, 4-bromophenol, 2,5-dibromo-1-(2-hydroxyethyl)benzene, 2-bromobenzyl alcohol, 3-bromobenzyl alcohol, 4-bromobenzyl alcohol, 4-hydroxyphenylboronic acid, 4-(hydroxymethyl)phenylboronic acid, 3-(hydroxymethyl)phenylboronic acid, 2,6-dibromo-4-(2-hydroxyethyl)-pyridine, 2,6-dibromo-3-(2-hydroxyethyl)pyridine, (S)-2,6-dibromo-4-(1-hydroxyethyl)pyridine, (R)-2,6-dibromo-4-(1-hydroxyethyl)pyridine, 2,6-dibromo-4-(hydroxymethyl)-pyridine, 2,6-dibromo-3-(hydroxymethyl)-pyridine, 2,6-dibromo-3-(3-hydroxypropyl)-pyridine, 3,6-dibromo-9H-2-hydroxycarbazole, 3,6-dibromo-9H-4-hydroxycarbazole, 2,7-dibromo-9-hydroxyfluorene, 2,7-dibromo-9-hydroxymethylfluorene, 1,4-dibromo-2-naphthol, 1,4-dibromo-2-naphthalenemethanol and 4,7-dibromo-2-hydroxybenzothiazole; when such a homocyclic or heterocyclic aromatic compound represented by the structural formula (III) is not commercially available, it may be produced by inserting the X and/or Y substituent onto a readily available hydroxyl-containing compound with the structural formula Ar-LH, e.g. through chlorination, bromination, iodination or boronation, using synthetic procedures known in the art.

In a preferred embodiment of the present invention, the polymers and copolymers of this invention may be produced via a reductive coupling reaction such as, but not limited to, Rieke coupling (e.g. following a procedure analog to the one disclosed in T.-A. Chen, R. D. Rieke, *J. Am. Chem. Soc.* (1992) 114, 10087), McCullough coupling (e.g. following a procedure analog to the one disclosed in R. D. McCullough et al., *J. Chem. Soc., Chem. Commun.*, 1992. 70 or U.S. Pat. No. 6,166,172), Stille coupling (e.g. following a procedure analog to the one disclosed in Milstein, D.; Stifle, J. K. *J. Am. Chem. Soc.* 1978, 100, 3636 or D. Milstein, J. K. Stille, *J. Am. Chem. Soc.*, 1979, 101, 4992.), Suzuki coupling (e.g. following a procedure analog to the one disclosed in N. Miyaura, T. Yanagi, A. Suzuki, *Synth. Commun.*, 1981, 11, 513) or Yamamoto coupling (e.g. following a procedure analog to the one diclosed in T. Yamamoto, A. Morita, Y. Miyazaki, T. Maruyama, H. Wakayama, Z H. Zhou, Y. Nakamura, T. Kanbara, S. Sasaki and K. Kubota, *Macromolecules*, 1992, 25, 1214).

In a particular embodiment of the invention, the polymers according to the second aspect of this invention include homopolymers containing monomeric groups or repeating units represented by the structural formula (IA) or the structural formula (IIA), and copolymers comprising two or more different recurring units, including a divalent group Ar', in a random or block arrangement type, which may include the same or a different aromatic homocyclic or heterocyclic group.

Suitable co-monomers that can be co-polymerised with the crosslinkable monomers according to different embodiments of the present invention, especially as represented by the structural formula (I) or the structural formula (II), include monomers, preferably conjugated monomers, comprising two reactive groups selected from the group consisting of halogen (e.g. I, Br or Cl), boronic acid, boronic esters, organotin, and other groups known by the person skilled in the art be useful in reductive coupling reactions. Those co-monomers includes monomers such as among others fluorene derivatives (such as but not limited to 2,7-dibromo-9,9-dialkylfluorene or 2,7-dibromo-9,9-diarylfluorenes (see e.g. C. Ego et al, *Adv. Mater.* 14 (2002) 809-811)), indenofluorene derivatives (see e.g. S. Setayesh, *Macromolecules* (2000)33: 2016), phenylene or ladder-type phenylene derivatives (see e.g. J. Grimme et al., *Adv. Mat.* (1995) 7, 292), aniline derivatives, thiophene derivatives (such as 2,5-dibromothiophenes and 2,5-dibromo-3-$C_{1-20}$ alkylthiophenes), fluorenone derivatives (such as but not limited to 2,7-dibromoflurenone), naphthalene derivatives (such as but not limited to 2,6-dibromonaphthalene and 1,4-dibromonaphthalene); anthracene derivatives (such as, but not limited to, 1,4-dibromoanthracene, 2,6-dibromoanthracene and 9,10-dibromoanthracene); furane derivatives (such as, but not limited to, 2,5-dibromofurane); pyrrole derivatives such as, but not limited to, 2,5-dibromopyrrole); 1,3,4-oxadiazole-2,5-dyil derivatives; 1,3,4-thiadiazole-2,5-diyl derivatives; 2,3-benzo[c]thienylene derivatives; thieno[3,2-b]thiophene-2,5-diyl derivatives; pyrrolo[3,2-b]pyrrole-2,5-diyl derivatives; pyrene derivatives such as, but not limited to, 2,7-dibromopyrene and 2,7-dibromo-4,5,9,10-tetrahydropyrene; 4,4'-biphenylene derivatives; phenanthrene derivatives (such as, but not limited to, 2,7-dibromo phenanthrene; 3,6-dibromophenanthrene and 2,7-dibromo,-9,10-dihydrophenantrene); dibenzo-furane-2,7-diyl derivatives; dibenzo-thiophene-2,7-diyl derivatives, and perylene derivatives (see C. Ego et al, *J. Am. Chem. Soc.* 125(2) (2003) 437-443).

A monomer or co-monomer involved in the polymerisation process in a Rieke or Yamamoto coupling polymerisation comprises preferably two identical (i.e. X=Y) reactive halogens (e.g. I, Br or Cl).

The monomer or co-monomers involved in a polymerisation process in a Suzuki coupling polymerisation preferably comprise:
(a) two identical (i.e. X=Y) reactive halogens (e.g. I, Br or Cl) for one molar half of the comonomers involved and two identical reactive groups selected from the group consisting of boronic acid and boronic esters for another molar half of the comonomers involved, or
(b) one reactive halogen (e.g. I, Br or Cl) and another reactive group (i.e. X and Y are different) selected from the group consisting of boronic acid or boronic esters.

The monomer or co-monomers involved in the polymerisation process in a Stille coupling polymerisation preferably comprise:
(a) two identical (i.e. X=Y) reactive halogens (e.g. I, Br or Cl) for one molar half of the comonomers involved and two identical reactive organotin groups for another molar half of the comonomers involved, or
(b) each one reactive halogen (e.g. I, Br or Cl) and another reactive (i.e. X and Y are different) organotin group.

The nature of the end groups resulting from the polymerisation process is usually difficult to determined in view of the large molecular mass of the polymer produced but it is usually accepted that they are either of the same nature as one of the leaving groups present on the starting monomer (e.g. halogen (e.g. I, Br or Cl), boronic acid, boronic ester or organotin, or hydrogen.

Methods to introduce alternative end-groups into the (co)polymer are well known to the person skilled in the art. A first method (a so-called "one pot" method) involves the addition of ending molecules together with the monomer or co-monomers into the reaction mixture right from the start of the polymerisation. A second method involves a first step of producing the (co)polymer as described in the previous paragraphs, and a second step of reacting this (co)polymer with the ending molecules. In both methods the ending molecules preferably comprise only one reactive halogen (e.g. I, Br or Cl), boronic acid, boronic ester, organotin or other group known by the person skilled in the art be useful in reductive coupling and are otherwise analog to the co-monomers described above.

An example of end-group introduction according to the first method is disclosed in C. Ego et al, *J. of the Am. Chem. Soc.* 125(2) (2003), 437-443).

According to a ninth aspect of the present invention the polymers according to the invention are suitable for use in active layer of organic devices and more particularly bulk heterojunction solar cells. The invention further relates to an active layer, which comprises the polymers according to the invention.

In order to be used as active layers, the polymers according to the invention are generally applied in the form of a thin film to a substrate by know methods familiar to the person skilled in the art, such as dipping, spin coating, inkjet printing, screen printing, etc.

The invention likewise relates to organic solar cells having one or more active layers, where at least one of these active layers comprises one or more polymers according to the invention.

The invention likewise relates to organic solar cells having one or more active layers, where at least one of these active layers is made from a blend of one or more polymers according to the invention having one type of electronic conductivity and a second semi-conducting material (small molecule as for example C60 derivatives or polymers as semi-conducting polymers) having the opposite type conductivity.

In a particular embodiment the second semi-conducting material having the opposite type conductivity may be or may not be a polymer according to the invention, i.e. with crosslinkable side groups.

Polymers according to the invention are furthermore suitable for organic based devices, for example but not limited to, for use in light emitting diodes, optical storage media, as photorefractive, for nonlinear-optical applications, in organic transistors such as Field effect transistors (FET), in photovoltaic cells (bi-layers, bulk heterojunction, tandem cells, dye-sensitized, organic/organic, organic/polymer, organic/inorganic, etc), in chemo- and bio-sensors.

According to another aspect of the present invention there is provided a method for stabilizing the nano-morphology of an active layer, which comprises one or more polymers according to the invention. The invention relates to a "stable" active layer, which comprises one or more polymers according to the invention. The nano-morphology of the active layer becomes stable after UV curing.

In a particular embodiment, UV lamps with shortwave (200-280 nm, typically 254 nm), midrange (280-315 nm, typically 302 nm) or long-wave (315-380 nm, typically 365 nm) are suitable for the UV-curing process which is carried out in inert atmosphere. The plurality of parameters of the UV light (for example but not limited to UV peak intensity and dosage) is controlled to ensure optimum curing of the layer. A low irradiation for a relatively long period is not equivalent to a higher irradiation for a shorter period, even if the overall energies are equal.

According to a fourth aspect of the present invention there is provided a time-stable organic solar cell comprising one or more "stable" active layer.

Organic solar cells with active layers containing one or more polymers according the invention are fabricated using state-of-the-art procedures as described in literature (especially relating to parameters such as substrates, electrodes, p-type/n-type ratios, solvents, concentration, etc). The active layer is preferably subject to an annealing step at a temperature dependent upon the copolymer ratio used in the copolymer, before the top electrode is applied. The choice of top electrode (cathode), e.g. 20 nm Ca and 80 nm Al or 100 nm Ytterbium, has little effect upon the ageing characteristics of the solar cell, but affects the absolute value of the initial power efficiency. The solar cell is then exposed to UV light under inert atmosphere for a defined time to induce the crosslinking of the active layer and therefore the stabilization of the nano-morphology of the active layer.

In a particular embodiment, UV lamps with short-wave (200-280 nm, typically 254 nm), Midrange (280-315 nm, typically 302 nm) or long-wave (315-380 nm, typically 365 nm) are suitable for the UV-curing process which is carried out in inert atmosphere.

Preferred irradiation conditions are: Wavelength: 253.7 nm; Intensity: 250 µW/cm$^2$ at 15 cm & 14 mW/cm$^2$ at 2 cm with a distance lamp/device during irradiation of 2 cm.

The following examples are given for illustrative purposes and, although explained in details with reference to various schemes showing 2,5-thienyl as the Ar or Ar' group, can easily translated by the skilled person to other Ar groups such as phenyl, naphthyl, pyrrolyl, pyridyl, carbazolyl, fluorenyl and benzothiazolyl, by mere analogy to the teaching incorporated therein.

General Experimental Materials and Methods

All chemicals were used as obtained from commercial sources, unless stated otherwise. THF and diethylether were distilled after drying with sodium wire and benzophenone until a blue colour appeared. 3-Bromothiophene was purified using short path distillation. NMR spectra were recorded on a Varian Inova 300 spectrometer at 300 MHz for $^1$H and at 75 MHz for $^{13}$C NMR using a 5 mm probe. Deuterated CHCl$_3$ was obtained from Cambridge Isotope Laboratories, Inc. $^1$H and $^{13}$C chemical shifts were reported downfield from tetramethylsilane (TMS) using the peak of residual CHCl$_3$ as an internal standard at δ=7.24 ppm. UV-Vis spectra were recorded using films dropcast from a CHCl$_3$ solution on a quartz substrate on a Varian CARY 500 UV-Vis-NIR spectrophotometer from 200 to 800 nm at 600 nm/min. Fourier transform infrared (FT-IR) was performed on a Perkin Elmer Spectrum One FT-IR spectrometer with a nominal resolution of 4 cm$^{-1}$. Samples for the FTIR were pellets in KBr or films dropcast from a CHCl$_3$ solution. Gas chromatography/mass spectrometry (GC-MS) was carried out on TSQ-70 and Voyager mass spectrometers. Size exclusion chromatography (SEC) was performed on a 1 wt % polymer solution, which was filtered with a 0.45 µm pore PTFE syringe filter. A Spectra series P100 (Spectra Physics) pump equipped with two mixed-B columns (10 µm, 2×30 cm, Polymer Labs) and a refractive index detector (Shodex) at 40° C. in THF at a flow rate of 1.0 ml/min were used. Molecular weight distributions were measured relative to polystyrene standards. Toluene was used as a flow rate marker.

The morphology of thin films, prepared analogously to the active layer of the solar cells, was studied with a transmission electron microscope (TEM) (Philips CM12-STEM). Thin freestanding films were used as TEM samples and obtained by spincoating a blend on a Silicon plate, covered with a thin layer of silicon oxide. These blends were separated from the silicon substrate by dissolving the oxide layer in HF and placed on a cupper grid.

For every accelerated lifetime measurement, a new substrate with 4 solar cells was used. The displayed $J_{sc}$ was the averaged $J_{sc}$ of the 4 solar cells. To obtain a continuous degradation curve, outliers were removed. The influence of a prolonged thermal treatment on the photovoltaic performance of the devices was measured in a set-up that measured Solar cell characteristics ($J_{sc}$, $V_{sc}$, FF, Eft) was measured every 30 minutes. Illumination was done with a White 5500K LED (Lamina) while the samples were kept under continuous annealing. In between the measurements, the samples were kept in the dark.

Monomer Synthesis

Synthesis of 3-Hexylthionphene (1)

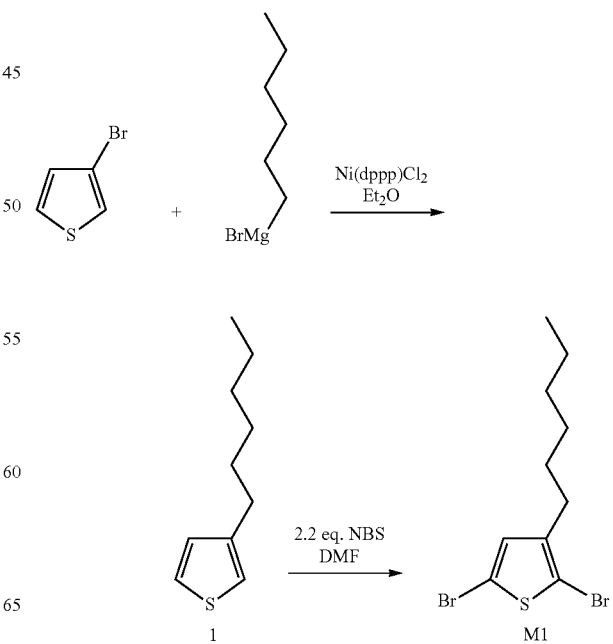

Starting from the commercially available products 3-bromothiophene (3-BT) and hexylmagnesiumbromide, 1 was produced using a Ni catalyst. In a three-necked flask, 100 ml (1 eq, 166.0 g, 1.018 mol) of bromothiophene is stirred under nitrogen atmosphere with 0.01 equivalent of Ni(dppp)Cl$_2$ (5.19 g, 0.0102 mol) and 300 ml dry diethylether. 1.2 equivalent (0.611 l of a 2.0M solution in diethyl ether, 1.22 mol) of hexylmagnesiumbromide was added dropwise at a temperature of 0° C. The reaction was stirred overnight at room temperature before neutralisation by addition of a 1M HCl solution. After extraction with diethyl ether, washing with a saturated NaHCO$_3$ solution and drying over MgSO$_4$ a brown liquid was obtained. This liquid was purified by short path distillation to obtain 1 in a yield of 95.6% (163.73 g, 0.973 mol) at p=7.10$^{-3}$ mbar and T=81-84° C.

Characterization: TLC (hexane): $R_f$=0.81; $^1$H NMR (300 MHz, CDCl$_3$): δ 7.23 (s, H), 6.95 (d, H), 6.92 (d, H), 2.63 (t, CH$_2$), 1.63 (q, CH$_2$), 1.32 (m, 3CH$_2$), 0.90 (t, CH$_3$); $^{13}$H NMR (75 MHz, CDCl$_3$): δ 142.8, 130.8, 110.2, 107.2, 31.5, 29.4, 29.3, 28.7, 22.5, 14.0; GC/MS (m/z): 168 [M]$^+$, 153 [M-CH$_3$]$^+$, 139 [M-CH$_2$CH$_3$]$^+$, 125 [M-(CH$_2$)$_2$CH$_3$]$^+$, 111 [M-(CH$_2$)$_3$CH$_3$]$^+$, 97 [M-(CH$_2$)$_4$CH$_3$]$^+$, 85 [M-(CH$_2$)$_5$CH$_3$]$^+$; FT-IR: 3000-2800 cm$^{-1}$ (C—H stretch alkyl), 1600-1500 cm$^{-1}$ (C=C stretch aromatic ring).

Synthesis of 2,5-dibromo-3-hexylthiophene (M1)

A solution of NBS (2.2 eq, 23.26 g, 0.130 mol) in 100 ml DMF was added dropwise to a solution of 1 (10 g, 0.059 mol) in 100 ml DMF and stirred in the dark at 0° C. When addition was complete, the reaction was allowed to warm to room temperature. After stirring for 48 h, the solution was added to 100 ml of an ice cooled 2.5M NaOH solution and stirred before extraction with 3×100 ml diethyl ether. The organic phase was washed using 100 ml of 2.5M NaOH solution, H$_2$O and NaCl$_{sat}$ and dried with MgSO$_4$ to obtain a yellow liquid that was purified using short path distillation to yield 81% (15.50 g, 0.048 mol) of a colourless liquid.

Characterization $^1$H NMR (300 MHz, CDCl$_3$): δ 6.76 (s, H), 2.49 (t, CH$_2$), 1.53 (q, CH$_2$), 1.29 (m, 3CH$_2$), 0.89 (t, CH$_3$); GC/MS (m/z): 326 [M]$^+$, 255 [M-(CH$_2$)$_4$CH$_3$]$^+$, 247 [M-Br]$^+$, 177 [M-Br, (CH$_2$)$_4$CH$_3$]$^+$, 111 [M-(CH$_2$)$_3$CH$_3$]$^+$, 95 [M-2Br, (CH$_2$)$_4$CH$_3$]$^+$. FT-IR: 3000-2800 cm$^{-1}$ (C—H stretch alkyl); 1600-1500 cm$^{-1}$ (C=C stretch aromatic ring).

2,5-dibromo-3-ethanolthiophene (2)

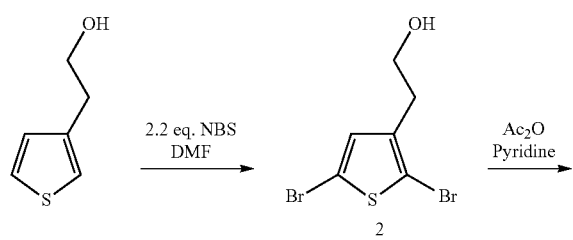

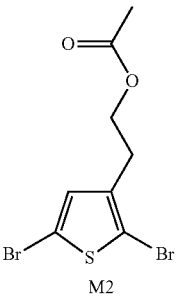

2 Was obtained by dibromination of 3-ethanolthiophene using NBS in an analogous procedure to that used for M1. 2.2 eq of NBS (32.93 g, 0.185 mol) was dissolved in 100 ml DMF and added dropwise to 3-ethanolthiophene (1 eq, 10.75 g, 0.084 mol) in 100 ml DMF at 0° C. The reaction was allowed to warm to room temperature and stirred for 48 h. The solution was added to 100 ml of an ice cooled 2.5M NaOH solution and stirred before extraction with 3×100 ml diethyl ether. The organic phase was washed with 100 ml of a 2.5M NaOH solution, H$_2$O and NaCl$_{sat}$, and dried with MgSO$_4$. The yellow liquid obtained was purified using short path distillation to isolate a colourless liquid (18.66 g, 73.5 mmol, 95%) at p=4.10$^{-3}$ mbar, T=107° C. $^1$H-NMR (300 MHz; CDCl$_3$;): δ 6.82 (s, 1H), 3.72 (t, 2H), 2.73 (t, 2H), 2.52 (s, 1H); $^{13}$C-NMR (75 MHz, CDCl$_3$): δ 139.0, 131.2, 110.7, 109.3, 61.5, 32.2; GC/MS m/z 288, 286, 284 [M]$^+$ 257, 255, 253 [M-CH$_2$OCH]$^+$ 257, 255, 253 [M-CH$_2$OC(O)CH$_3$]$^+$ 189, 187 [M-Br, OCOCH$_3$]$^+$ 2,5-dibromo-3-acetylethanolthiophene (M2)

M2 was obtained after stirring 2 (1 eq, 36.2 g, 0.143 mol) under reflux with 1.3 eq. (18.93 g, 0.185 mol) of acetic anhydride and 140 ml of pyridine for 5 hours. The mixture was neutralised by adding HCl, extracted with 3×100 ml diethyl ether and washed with 3×100 ml H$_2$O. The extract was dried over MgSO$_4$, filtered and evaporated. The mixture was purified with short path distillation to provide 36.2 g (113 mmol, 78%) of M2 at p=1.10$^{-3}$ mbar and T=95° C.

Characterization: TLC (hexane:diethyl ether, 8:2) $R_f$=0.81, $^1$H-NMR (300 MHz, CDCl$_3$): δ 6.79 (s, 1H), 4.17 (t, 2H), 2.82 (t, 2H), 2.02 (s, 3H); $^{13}$C-NMR (75 MHz, CDCl$_3$): δ 170.7, 138.1, 130.8, 110.7, 109.6, 62.8, 28.7, 20.8; GC/MS (m/z) 330, 328, 326 [M]$^+$ 270, 268, 266 [M-OCOCH$_3$]$^+$ 257, 255, 253 [M-CH$_2$OC(O)CH$_3$]$^+$ 205, 207 [M-Br]$^+$ 187, 189 [M-Br, OCOCH$_3$]$^+$ 176, 174 [M-Br, CH$_2$OC(O)CH$_3$]$^+$ 108 [M-2Br, CH$_2$OC(O)CH$_3$]$^+$, 95 M-2Br, CH$_2$CH$_2$OC(O)CH$_3$]$^+$ $\nu_{max}$(film)/cm$^{-1}$ Polymer Synthesis Example 1 (Comparative)

Synthesis of poly(3-hexyl-thiophene) (P3HT)

P3HT for use in a solar cell as a reference system was synthesized using the Rieke method for the production of highly regioregular poly(3-alkylthiophene)s. A solution of M1 (1 eq, 10.04 g, 0.031 mol) in 80 ml THF was added to active Zinc at −78° C. The organozinc solution formed was added to a solution of 0.002 eq (0.035 g, 6.4 10$^{-5}$ mol) Ni(dppp)Cl$_2$ in 40 ml THF and stirred under inert atmosphere at 60° C. for 18 h. The crude polymer was precipitated in a MeOH/2M HCl (2/1, v/v) mixture and purified by solid phase extraction with methanol and hexane. The purified polymer was extracted with chloroform and precipitated in MeOH before filtration and drying, yielding 3.63 g (67%) of conjugated polymer.

GPC (THF): $M_n$=27,800; $M_w$=53,500; polydispersity index, D=1.9;

Example 2

Synthesis of random copolymers of 3-hexylthiophene (M1) and 3-(2-acetoxyethyl)thiophene (M2) (P1), random copolymers of 3-hexylthiophene and 3-hydroxyethylthiophene (P2), and random copolymers with a 9:1 molar ratio of 3-hexylthiophene and 3-cinnamoyloxyethylthiophene (P3)

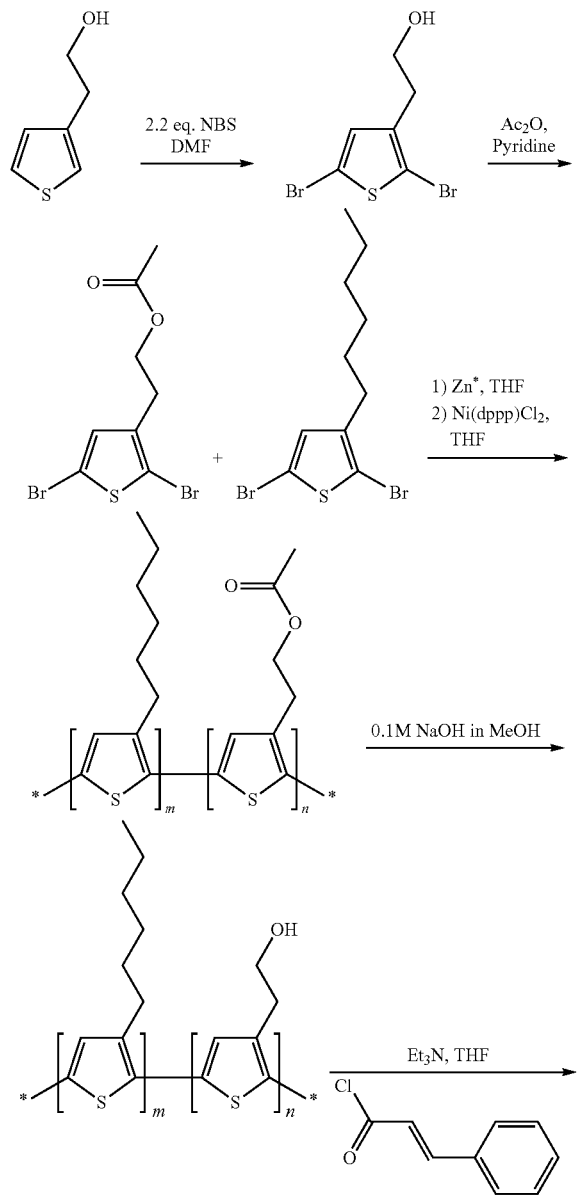

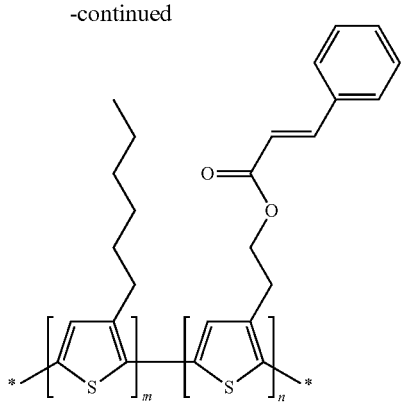

a) Synthesis of poly-3-hexylthiophene-co-3-(2-acetoxyethyl)thiophene (P1)

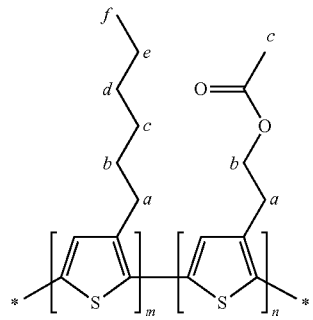

A solution of a mixture of 2,5-dibromo-3-(2-acetoxyethyl)thiophene (M2) (10% molar) (1.05 g, 0.003 mol) and 2,5-dibromo-3-hexylthiophene (M1) (90% molar) (9.41 g, 0.029 mol) in THF was added to active zinc at −78° C. to form an organozinc solution which was then polymerised in the presence of a Ni(dppp)Cl$_2$ catalyst. After reaction, the co-polymer was precipitated in a mixture of MeOH and 2M HCl (2/1). The crude co-polymer was purified using a soxhlet extraction with methanol and pentane. The purified poly-3-hexylthiophene-co-3-(2-acetoxyethyl)thiophene (P1) was extracted with chloroform and precipitated again in MeOH, before filtration and drying to obtain 3.18 g of a 9/1 copolymer in 61% yield, which was characterised as follows:

GPC (THF): $M_n$=34,400; $M_w$=65,500; polydispersity index, D=1.9 giving an average of 207 repeating units/chain;

$^1$H-NMR (CDCl$_3$): δ=7.00 (1H$_{arom,AcET}$, s), 6.96 ppm (1H$_{arom,3HT}$, s), 4.35 ppm (2H$_{b,AcET}$, t), 3.14 ppm (2H$_{arom,AcET}$, t), 2.79 ppm (2H$_{a,3HT}$, t), 2.05 ppm (3H$_{c,AcET}$, s) 1.70 ppm (2H$_{b,3HT}$, t), 1.45 ppm (2H$_{c,3HT}$, m), 1.40 ppm (2H$_{d,3HT}$, m), 1.35 ppm (2H$_{e,3HT}$, m), and 0.90 ppm (3H$_{f,3HT}$, t);

UV/Vis: λmax at 555 nm; sh at 600 nm;
infrared spectrum: see Table 1 below.

b) Synthesis of poly-3-hexylthiophene-co-3-(2-hydroxyethyl)thiophene (P2)

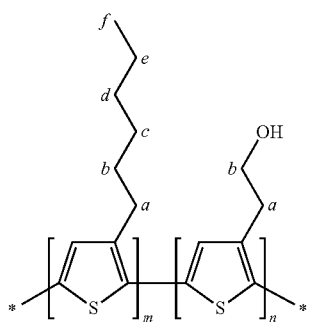

1.04 g Polymer (P1) was refluxed under an inert atmosphere with 100 mL of 0.1 M NaOH solution in MeOH to yield P2 in 100% yield, which was characterised as follows:

GPC (THF): $M_n$=31,300, $M_w$=68,100, D=2.2 giving an average of 190 repeating units/chain;

$^1$H-NMR (CDCl$_3$): δ=7.03 (1H$_{arom,ET}$, s), 6.96 ppm (1H$_{arom,3HT}$, s), 3.94 ppm (2H$_{b,ET}$, t), 3.09 ppm (2H$_{a,ET}$, t), 2.79 ppm (2H$_{a,3HT}$, t), 1.70 ppm (2H$_{b,3HT}$, t), 1.45 ppm (2H$_{c,3HT}$, m), 1.40 ppm (2H$_{d,3HT}$, m), 1.25 ppm (2H$_{e,3HT}$, m), and 0.90 ppm (3H$_{f,3HT}$, t);

UV/Vis: λmax at 551 nm, sh, at 600 nm;
infrared spectrum: see Table 1 below.

c) Synthesis of poly-co-(3-hexylthiophene-co-3-cinnamoyloxyethylthiophene) (P3)

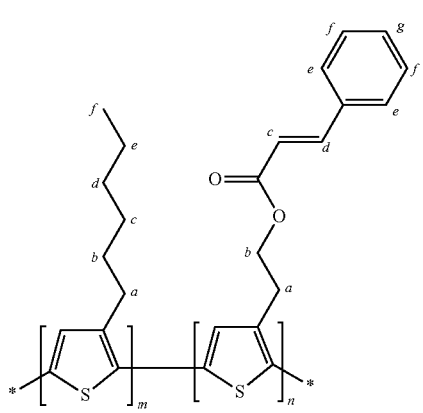

0.61 g P3 was obtained in 95% yield by reacting 0.60 g poly-3-hexylthiophene-co-3-(2-hydroxyethyl)thiophene (P2) with 0.62 g (0.004 mol) cinnamoyl chloride in THF in the presence of 0.37 g (0.004 mol) triethylamine, and was purified using soxhlet extraction with methanol and acetone before characterisation as follows:

GPC (THF): $M_n$=33,100, $M_w$=74,500, D=2.2 giving an average of 193 repeating units/chain;

$^1$H-NMR (CDCl$_3$): δ=7.67 ppm (1H$_{d,cin}$, d), 7.47 ppm ($^2$H$_{e,cin}$, m), 7.32 ppm (2H$_{f,cin}$, m), 7.05 ppm (1H$_{g,cin}$, m), 6.96 ppm (1H$_{arom,3HT\ and\ cin}$, s), 6.42 ppm (1H$_{c,cin}$, d), 4.49 ppm (2H$_{b,cin}$, t), 3.23 ppm ($^2$H$_{a,cin}$, t), 2.79 ppm (2H$_{a,3HT}$), 1.70 ppm (2H$_{b,3HT}$, m), 1.40 ppm (2H$_{c,3HT}$, m), 1.35 ppm (2H$_{d,3HT}$, m), 1.25 ppm (2H$_{e,3HT}$, m), and 0.90 ppm (3H$_{f,3HT}$, t); and integrations originating from the M2 monomer unit corresponded to about 10% of a comparable integration originating from the M1 monomer unit, indicating that 1 out of 10 monomer units has a functionalized side chain. Disappearance of the methyl group in the acetylester of the P1 side chain at δ=2.05 ppm proved hydrolysis was completed. The complete functionalisation was also illustrated by a change in chemical shift of CH$_2$—proton signals in P3 because of a different ester. Appearance of double bond and aromatic proton signals in the functionalized polymer confirmed the presence of the cinnamoyl ester in the side chain.

UV/Vis: λmax at 275 nm and 551 nm, sh. at 600 nm. λ$_{max}$ at 275 nm of polymer films dropcast from chloroform solutions was due to the presence of the cinnamic acid ester in the copolymer side chain. In the absorption region of the conjugated polymer, the shoulder at 600 nm had a higher intensity, but was less sharply pronounced. After 2 hours UV-exposure of such a film of P3 the intensity of the 275 nm peak decreased ca. 10% indicating that some cinnamoyl moieties had disappeared due to photo-initiated [2+2] cyclo-addition. With an average of about 200 monomer units in a polymer chain, there were thus an average of 2 side chains that were linked to another chain, which accounted for the immobilization and enhanced thermal stability after such exposure;

infrared spectrum: see Table 1 below.

TABLE 1

| | wavenumber (cm$^{-1}$) of absorptions observed in FT-IR | | | |
|---|---|---|---|---|
| Absorption: | P3HT homo-polymer (3) | 10% ester functionalised copolymer (P1) | 10% ethanol functionalised copolymer (P2) | 10% cinnamon functionalised copolymer (P3) |
| C—H stretch on aromatic ring | 2953 | 2952 | 2952 | 2950 |
| C—H stretch in aliphatic chain | 2923 | 2922 | 2922 | 2923 |
| C—H stretch in aliphatic chain | 2853 | 2853 | 2852 | 2853 |
| C=O stretch ester bond | — | 1742 | — | 1715 |
| Conjugated system | 1635 | 1635 | 1640 | 1635 |
| C=C asymmetric ring stretch | 1508 | 1507 | 1508 | 1505 |
| C=C symmetric ring stretch | 1454 | 1452 | 1455 | 1449 |
| methyl deformation | 1376 | 1376 | 1376 | 1375 |
| C—O stretch | — | 1225 | 1262 | 1259 |
| C—H in plane bending of 2,3,5 substituted thiophene | 1088 | 1032 | 1046 | 1075 |

TABLE 1-continued

| | wavenumber (cm$^{-1}$) of absorptions observed in FT-IR | | | |
|---|---|---|---|---|
| Absorption: | P3HT homo- polymer (3) | 10% ester functionalised copolymer (P1) | 10% ethanol functionalised copolymer (P2) | 10% cinnamon functionalised copolymer (P3) |
| C—H out of plane bending of 2,3,5 substituted thiophene or C—S stretching | 820 | 819 | 821 | 818 |
| methyl rock | 724 | 723 | 723 | 721 |

The C=O ester absorption at around 1740 cm$^{-1}$ in P1 disappeared upon its hydrolysis to P2. Upon functionalisation of P2 to P3 a peak at around 1715 cm$^{-1}$ appeared due to the C=O bond of the cinnamic ester group.

Example 3

Synthesis of random copolymers of 3-hexylthiophene and 3-cinnamoylaminoethylthiophene (P4)

The synthesis proceeds according to the following scheme and provides a copolymer comprising recurrent units from a monomer represented by the structural formula (I) wherein L is NH.

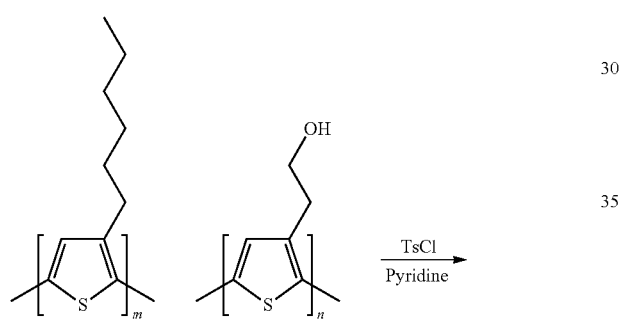

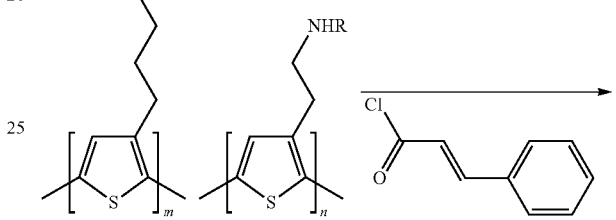

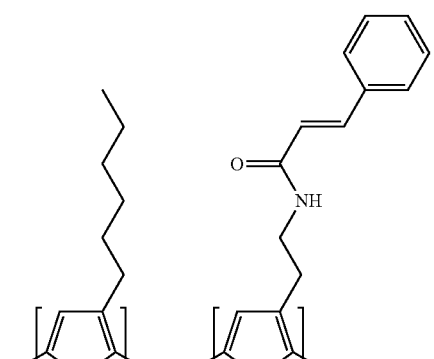

Example 4

Synthesis of random copolymers of 3-hexylthiophene and 3-cinnamoylthioethylthiophene (P5)

The synthesis proceeds according to the following scheme and provides a copolymer comprising recurrent units from a monomer represented by the structural formula (I) wherein L is S.

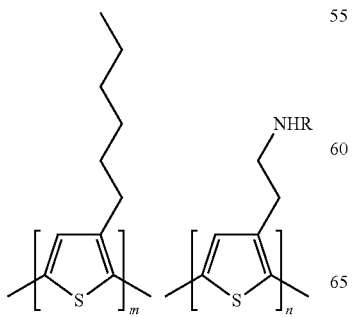

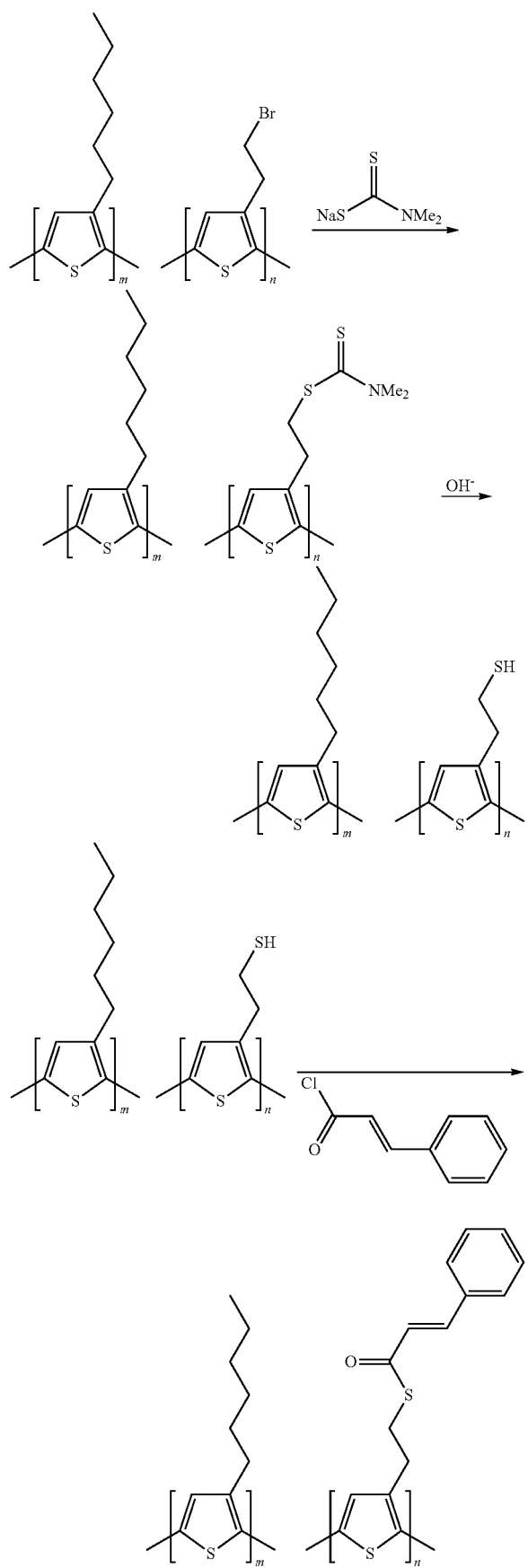

Example 5

Fabrication and Comparative Study of the Nano-Morpholgy of Two Active Layers Made Respectively of a Comparative Semi-Conducting Polymer P3HT (3) and a N-Type Material (Fullerene Derivative) for Film A, and the Random Copolymer (P3) of Example 2 and a n-type Material (Fullerene Derivative) for "Film B"

Figure 2:
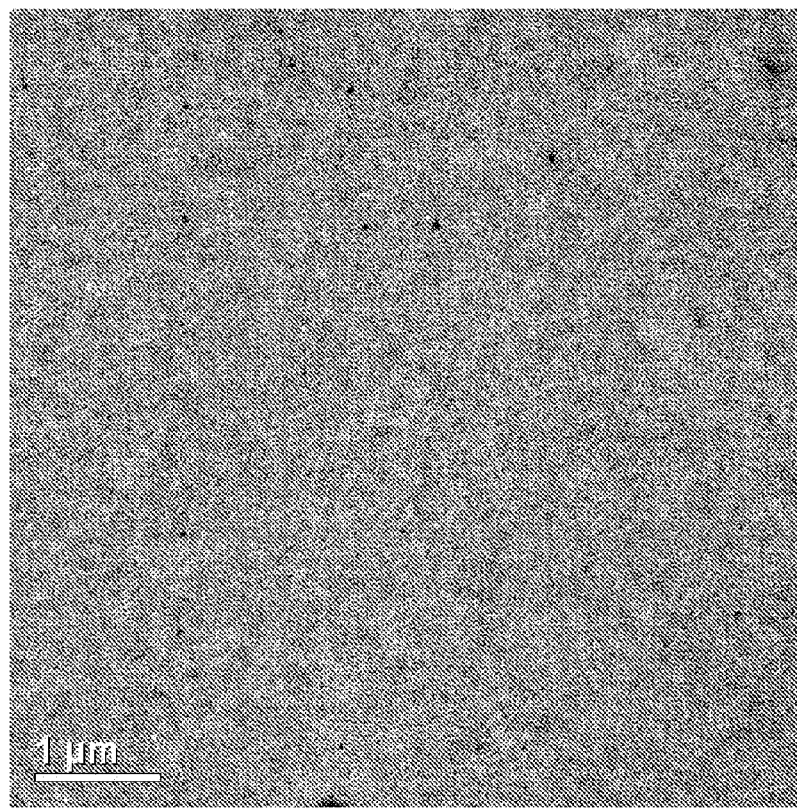
FIG. 2 shows a TEM picture of a comparative blend (film A) as deposited.
Figure 3:
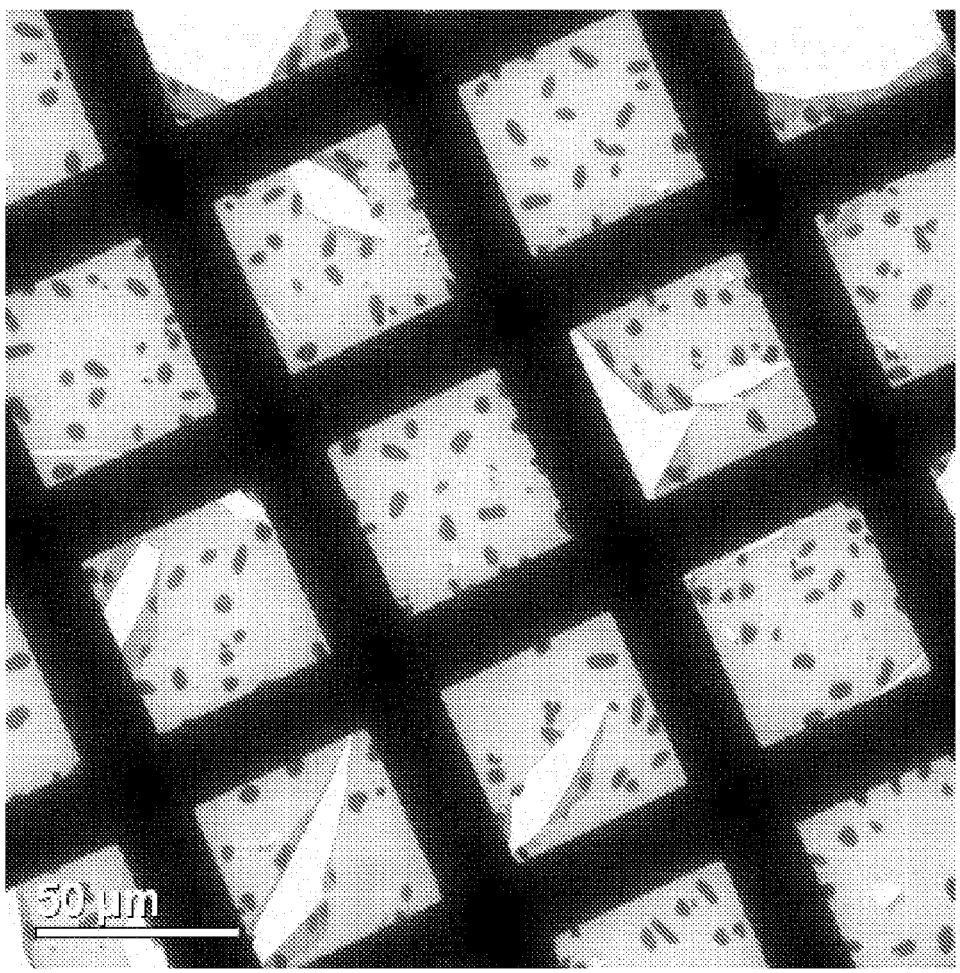
FIG. 3 shows a TEM picture of a comparative blend (film A) after heat treatment.
Figure 4:
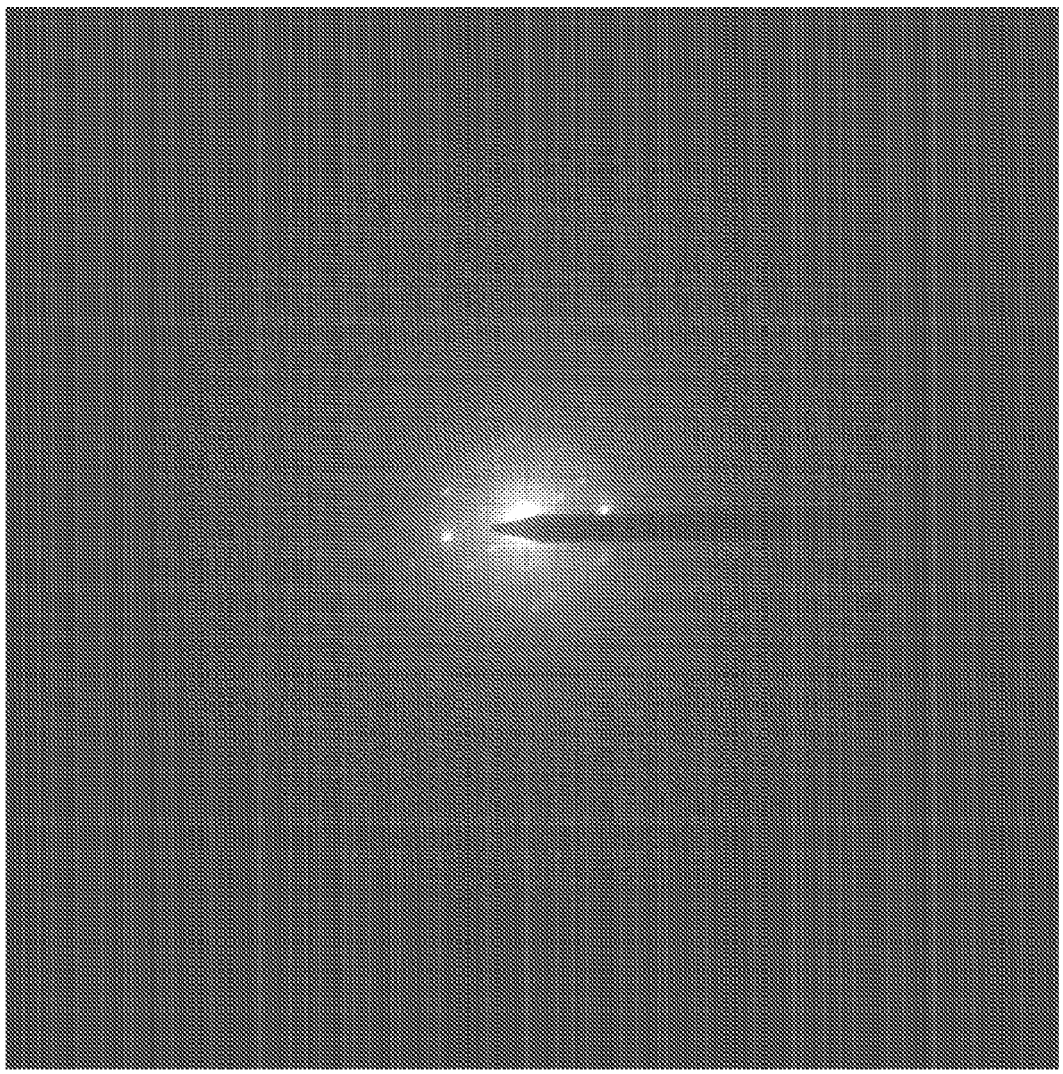
FIG. 4 shows as electron diffraction pattern measured on the comparative blend (FIG. 3) after heat treatment.
Figure 5:
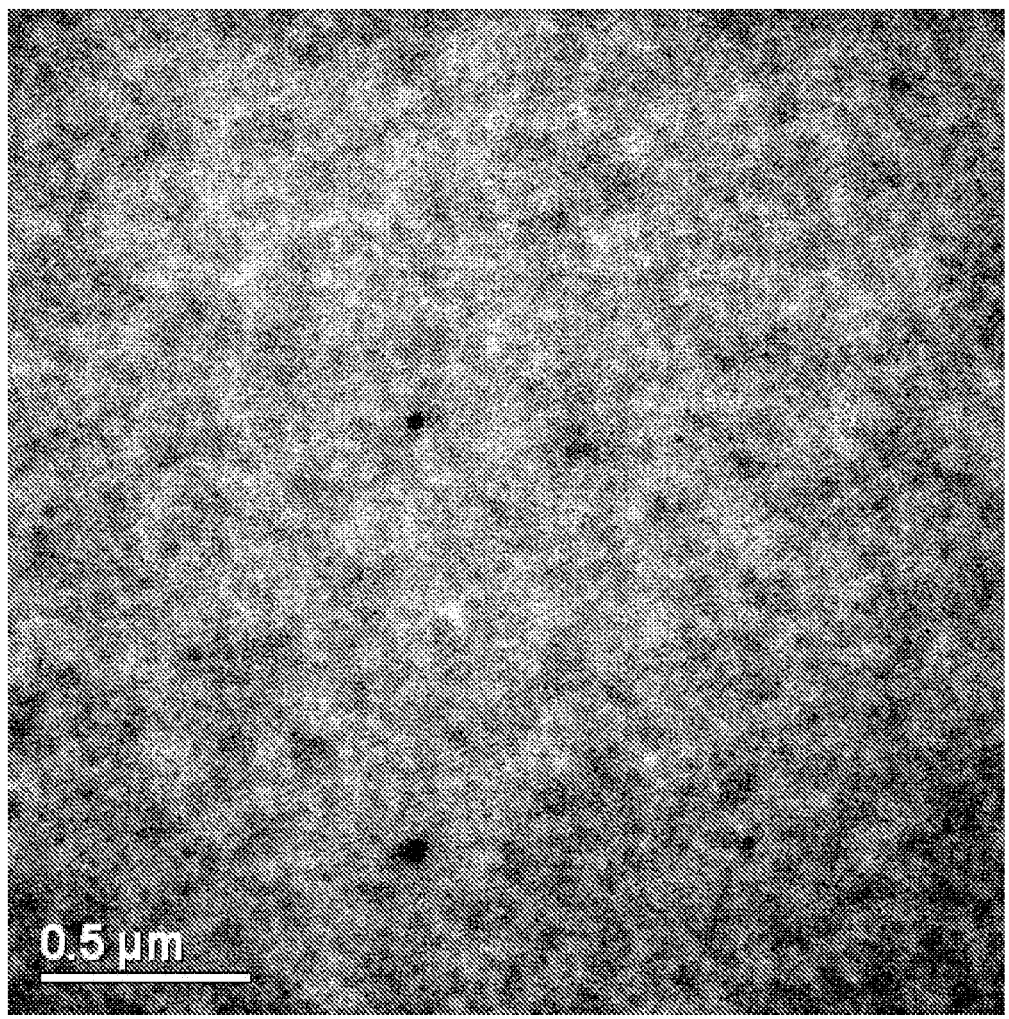
FIG. 5 shows a TEM picture of a comparative blend (film A) after heat treatment. The magnification is larger than in the TEM picture of FIG. 3.
Figure 6:
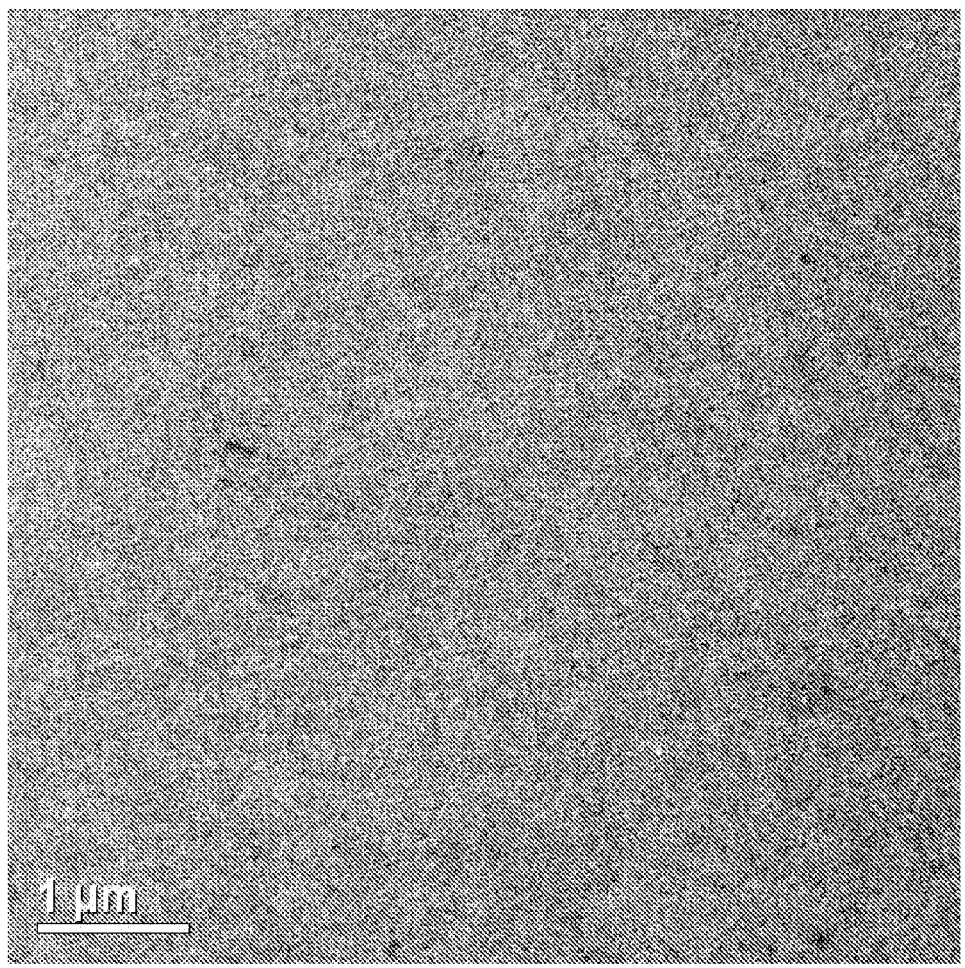
FIG. 6 shows a TEM picture of a blend according to an embodiment of the present invention (film B) as deposited.
Figure 7:
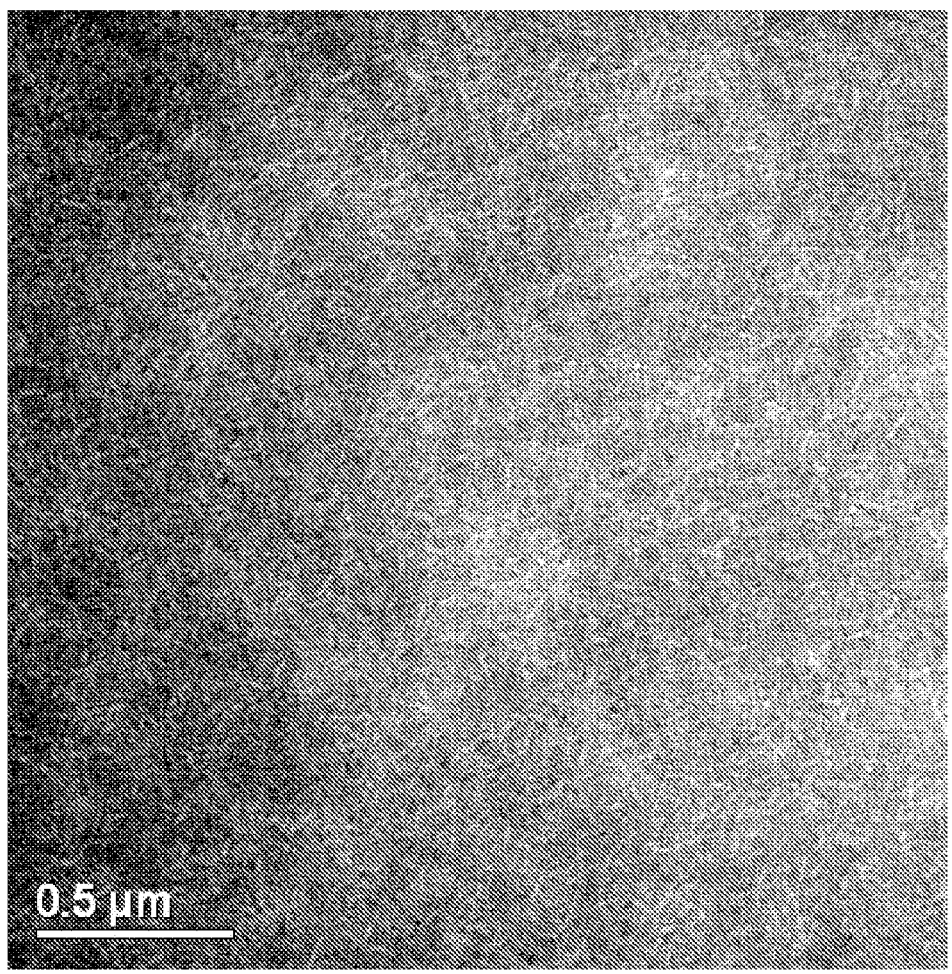
FIG. 7 shows a TEM picture of a blend according to an embodiment of the present invention (film B) after heat treatment.
Figure 8:
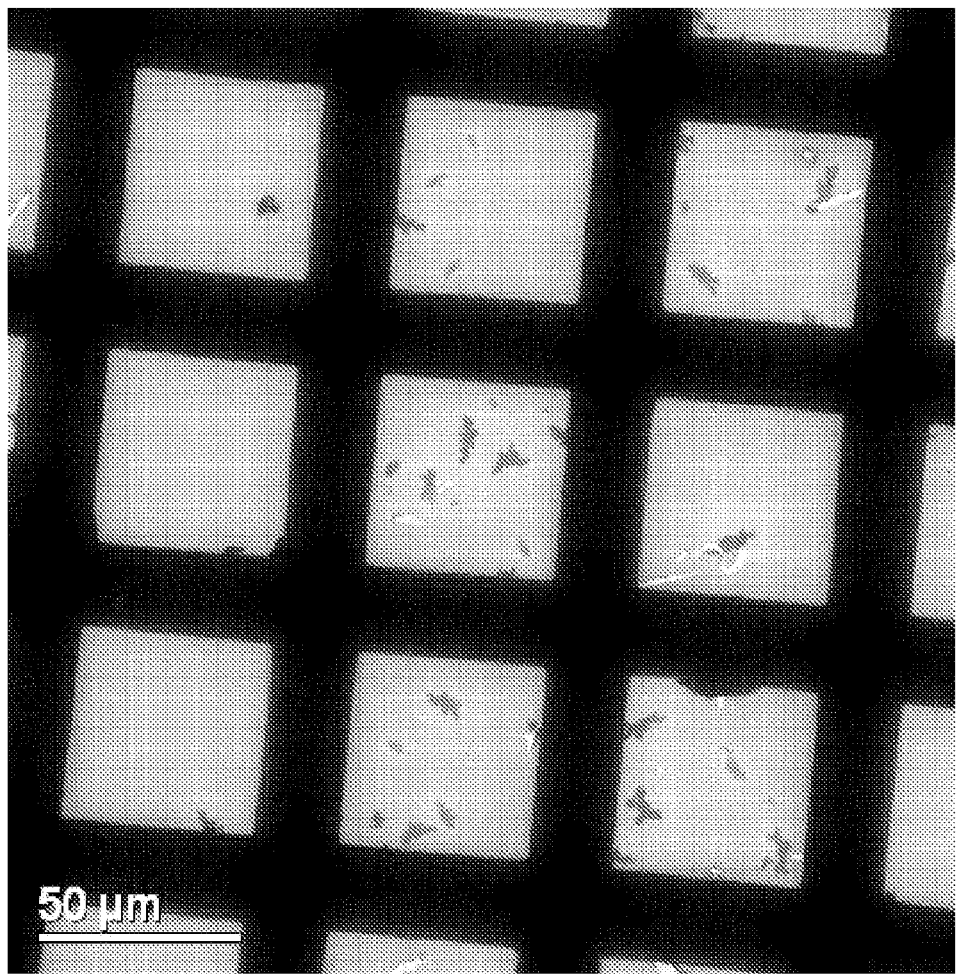
FIG. 8 shows a TEM picture of a blend according to an embodiment of the present invention (film B) after heat treatment. The magnification is smaller than for FIG. 7.
Figure 9:
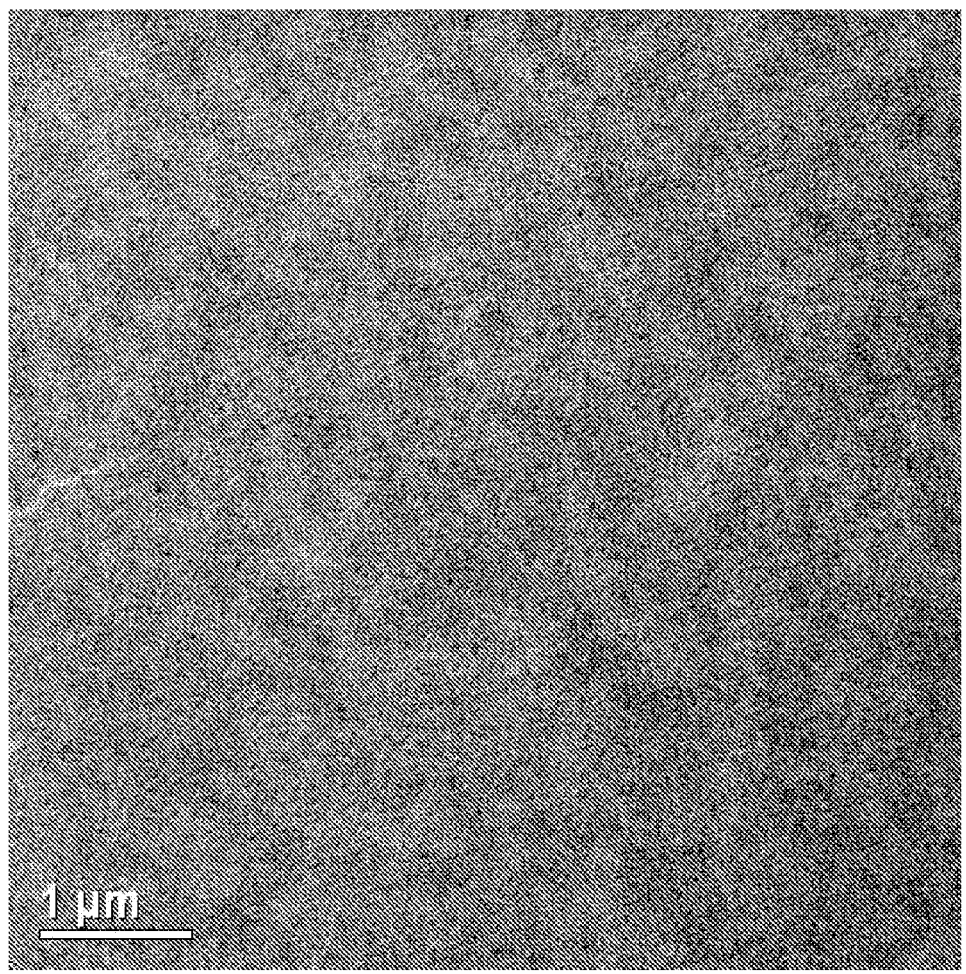
FIG. 9 shows a TEM picture of a blend according to an embodiment of the present invention (film B) after UV curing and heat treatment.
Figure 10:
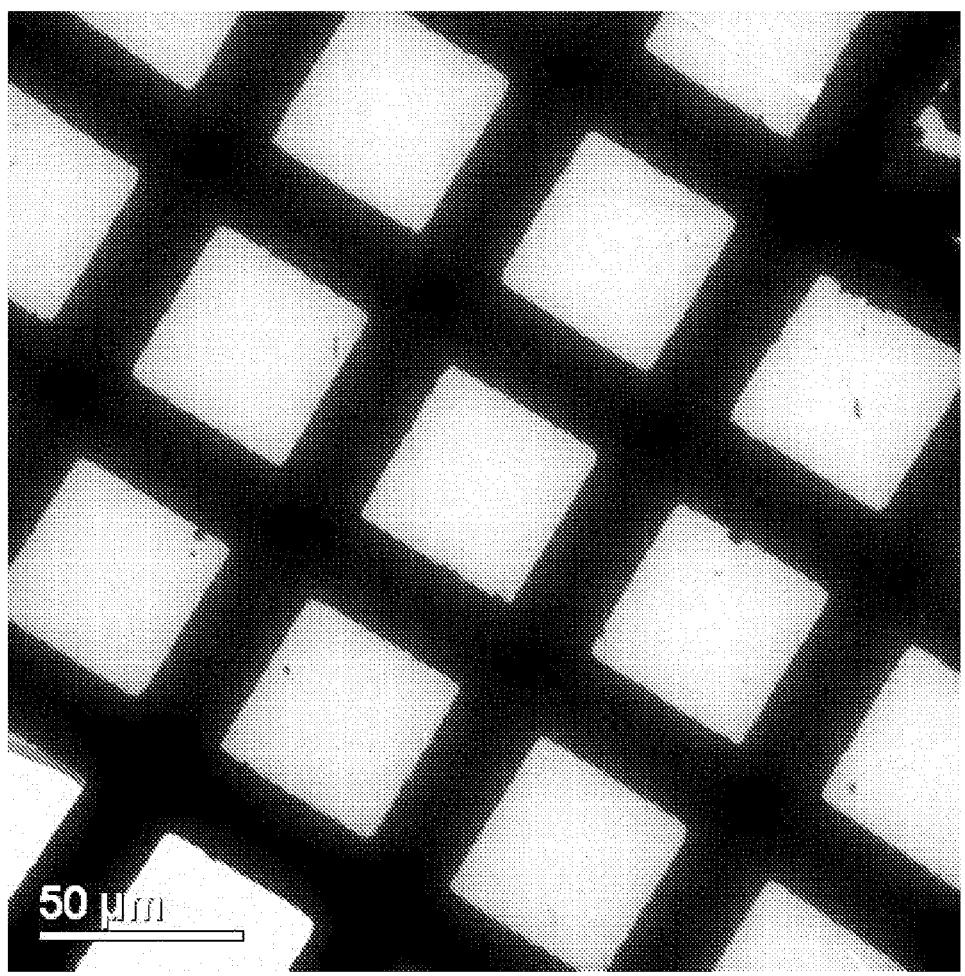
FIG. 10 shows a TEM picture of a blend according to an embodiment of the present invention (film B) after UV curing and heat treatment. The magnification is smaller than for FIG. 9.

In the TEM pictures of FIG. 7-8, a phase separation in the thin film B was observed after 2 hours at 110° C. This phase separation was similar to these observed for the film A heated in the same conditions (FIGS. 3 and 5). This phase separation was prevented when the thin film B was preliminarily UV cured: the nano-morphology of the film was then stable (FIG. 9-10). Film A and Film B as deposited, i.e. before heat treatment, are shown in FIGS. 2 and 6 respectively for comparison purpose. FIG. 4 shows an electron diffraction of a black spot as visible in FIG. 3. The diffraction pattern indicates that the black spots are PCBM crystals.

Example 6

Figure 11:
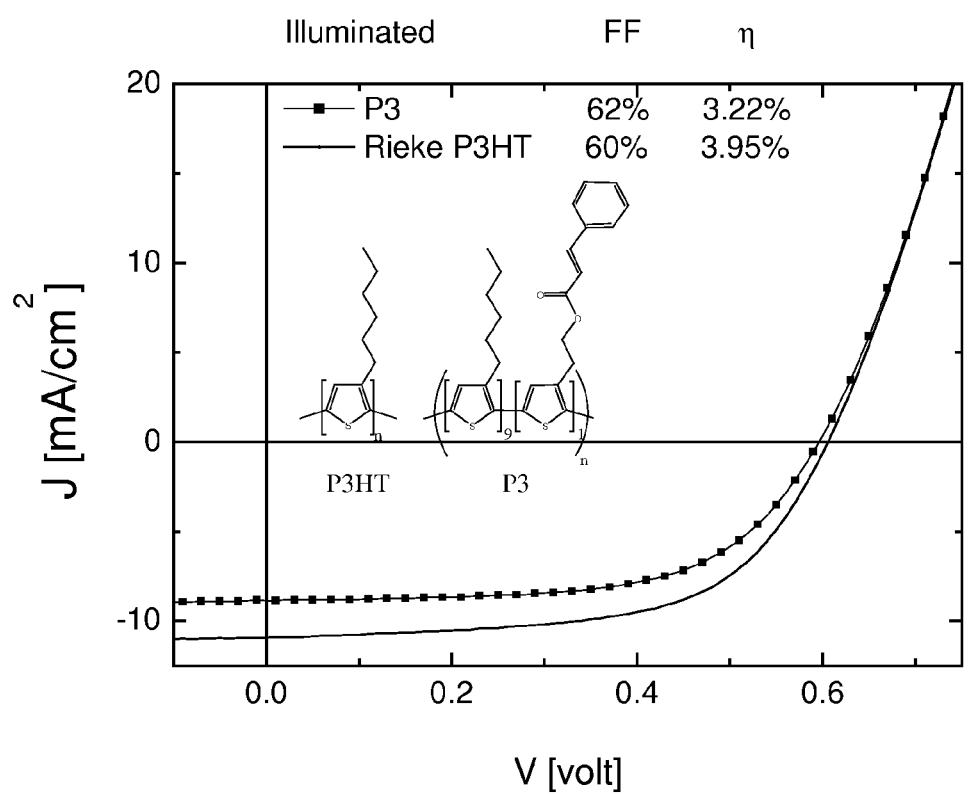
FIG. 11 is a graph of the current density versus the voltage as measured on a bulk heterojunction solar cell having an active layer made from a blend according to an embodiment of the present invention.
Figure 12:
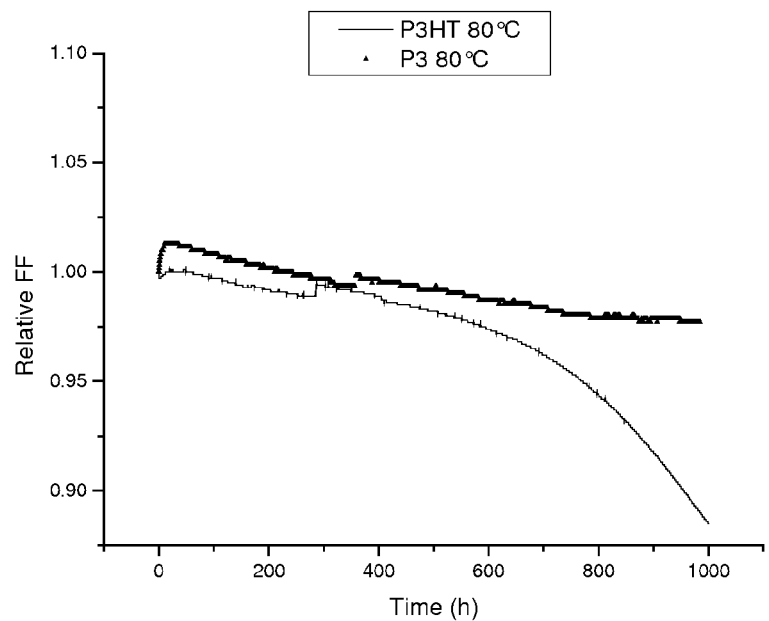
FIG. 12 is a graph of the relative Fill Factor versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 80° C.
Figure 13:
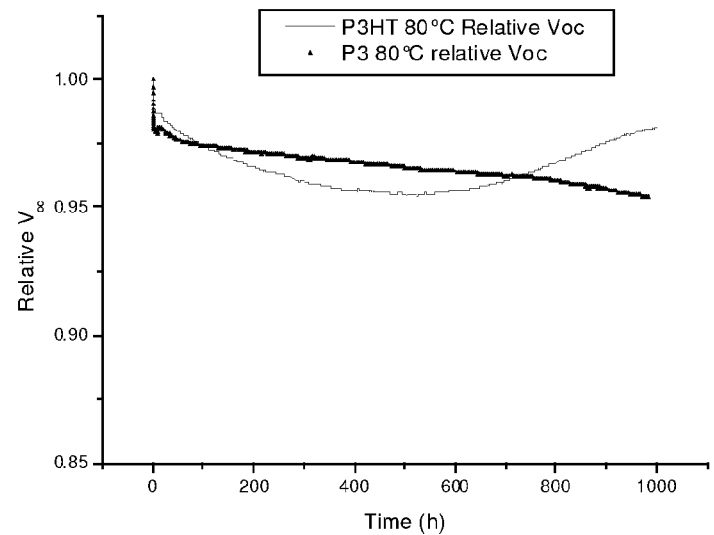
FIG. 13 is a graph of the relative open circuit voltage versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 80° C.
Figure 14:
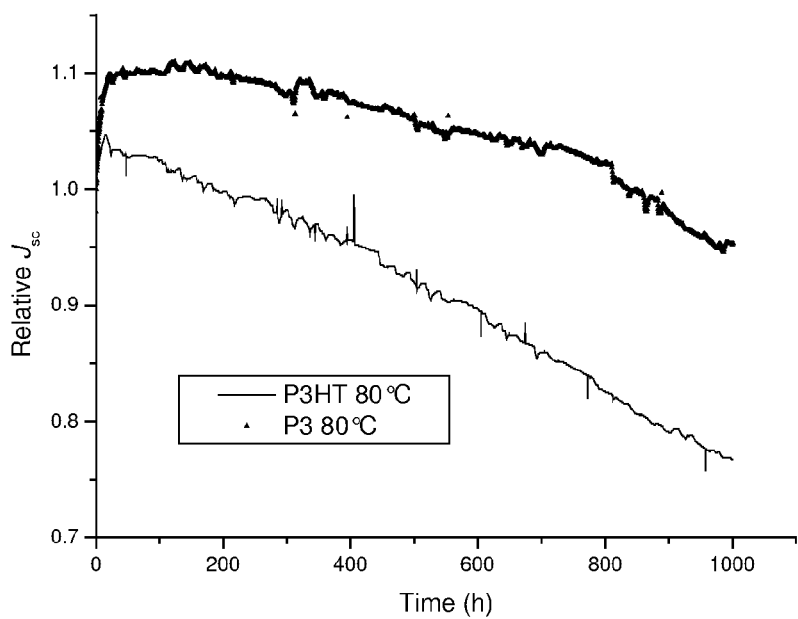
FIG. 14 is a graph of the relative short-circuit current density versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 80° C.
Figure 15:
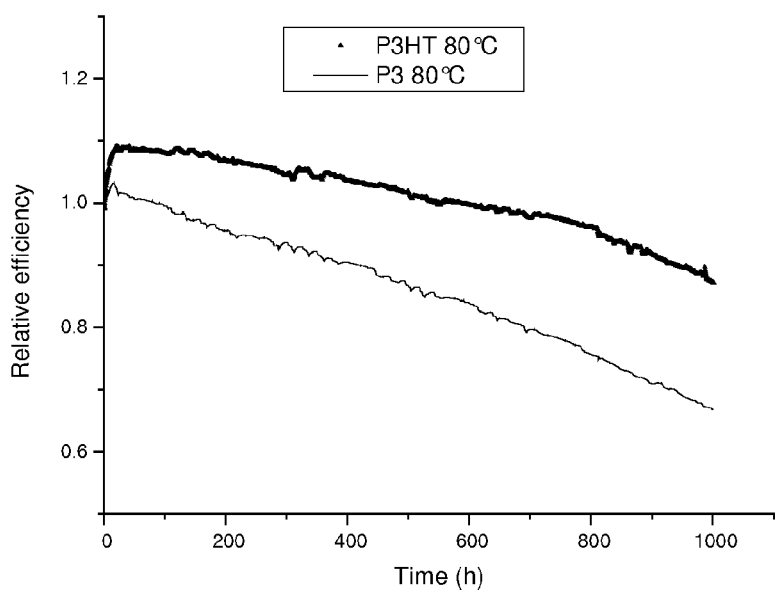
FIG. 15 is a graph of the relative power efficiency versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 80° C.
Figure 16:
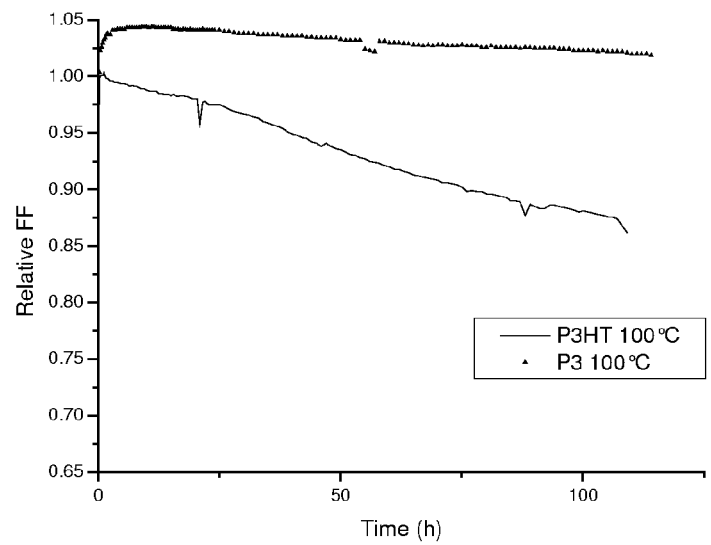
FIG. 16 is a graph of the relative Fill Factor versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 100° C.
Figure 17:
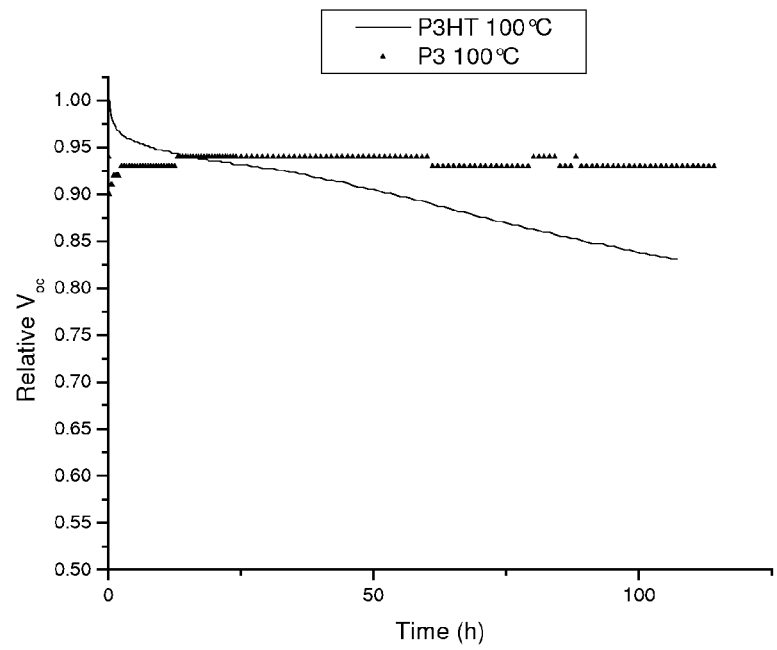
FIG. 17 is a graph of the relative open circuit voltage versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 100° C.
Figure 18:
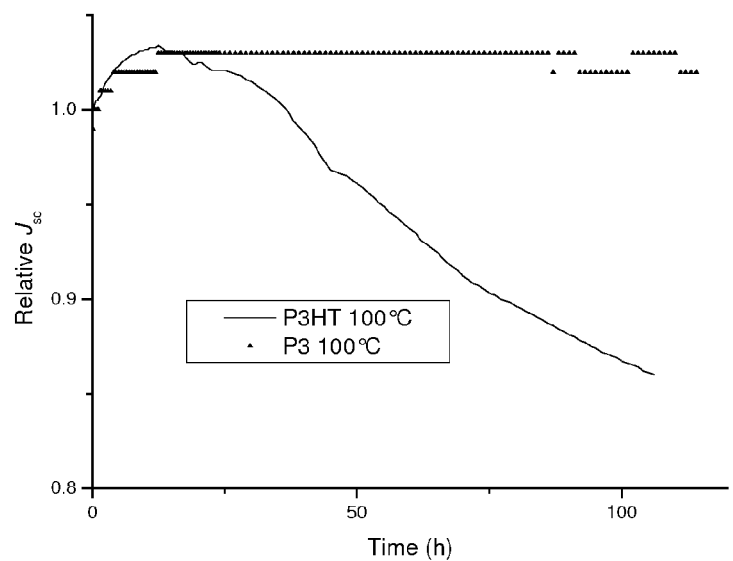
FIG. 18 is a graph of the relative short-circuit current density versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 100° C.
Figure 19:
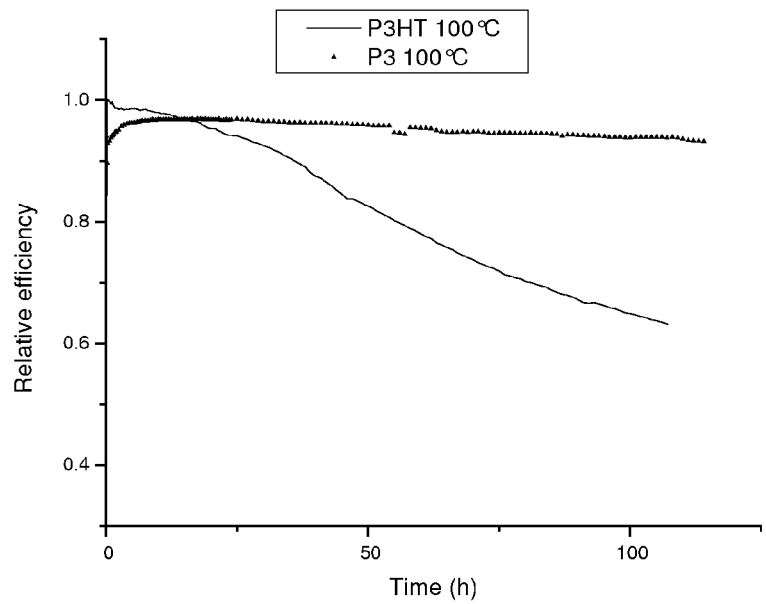
FIG. 19 is a graph of the relative power efficiency versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 100° C.
Figure 20:
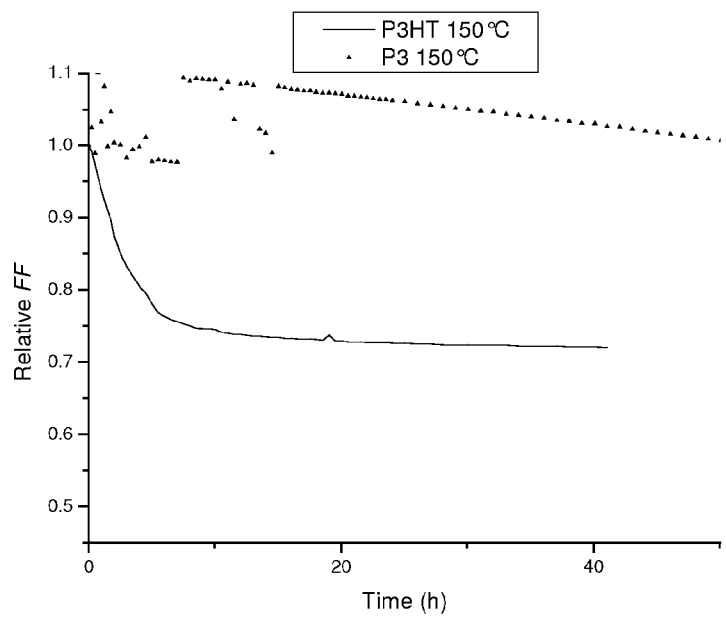
FIG. 20 is a graph of the relative Fill Factor versus time as measured on a bulk heterojunction solar cell having an active layer made from a comparative blend (Cell A) and on a bulk heterojunction solar cell having an active layer made from a blend according to an embodiment of the present invention (Cell B) at 150° C.
Figure 21:
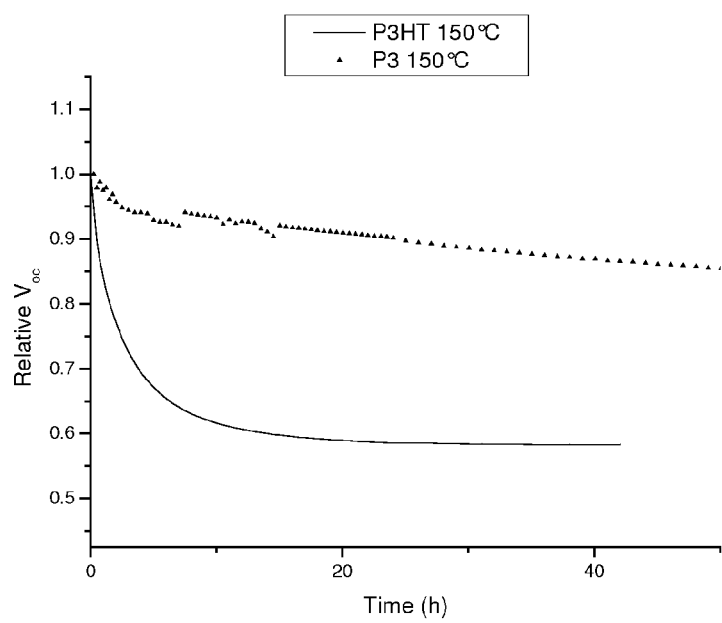
FIG. 21 is a graph of the relative open circuit voltage versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 150° C.
Figure 22:
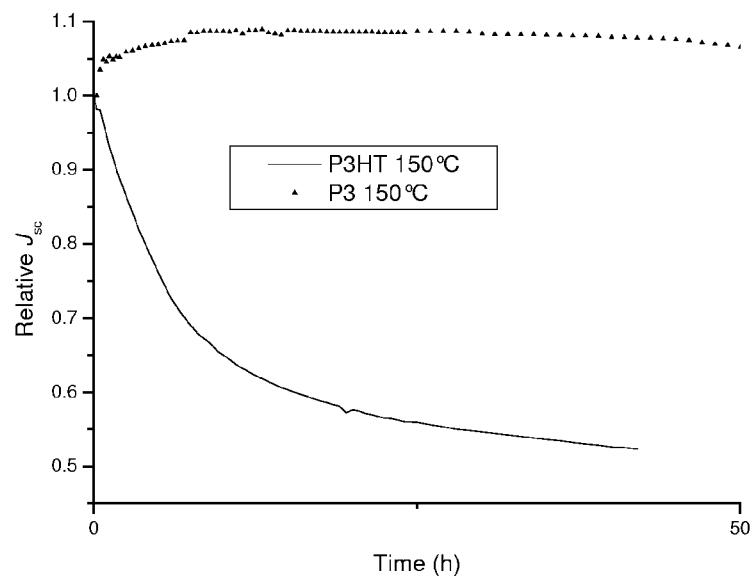
FIG. 22 is a graph of the relative short-circuit current density versus time as measured on a bulk heterojunction solar cell having an active layer made from a comparative blend (Cell A) and on a bulk heterojunction solar cell having an active layer made from a P3/PCBM blend according to an embodiment of the present invention (Cell B) layer made from a blend according to an embodiment of the present invention at 150° C.
Figure 23:
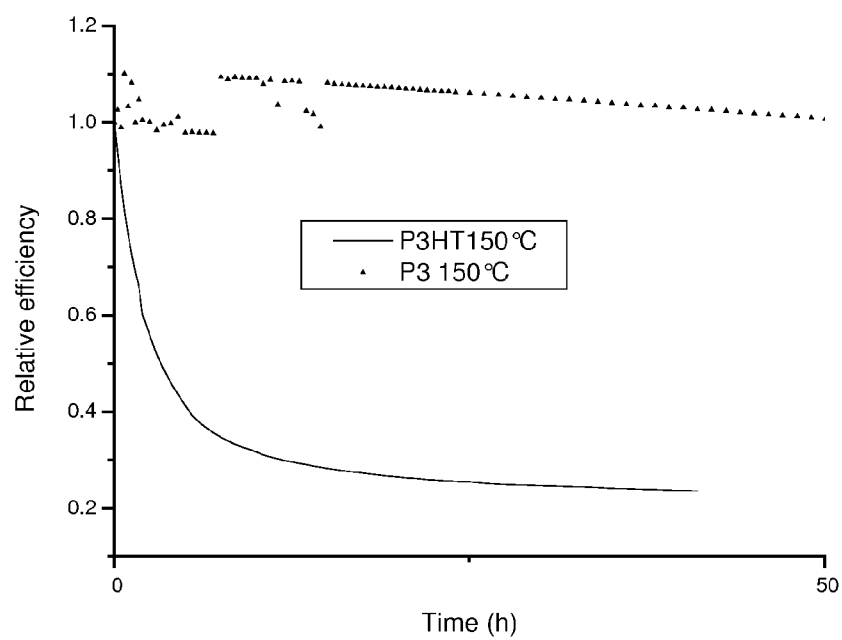
FIG. 23 is a graph of the relative power efficiency versus time as measured on a bulk heterojunction solar cell having an active layer made from a comparative blend (Cell A) and on a bulk heterojunction solar cell having an active layer made from a P3/PCBM blend according to an embodiment of the present invention (Cell B) at 150° C.
Figure 24:
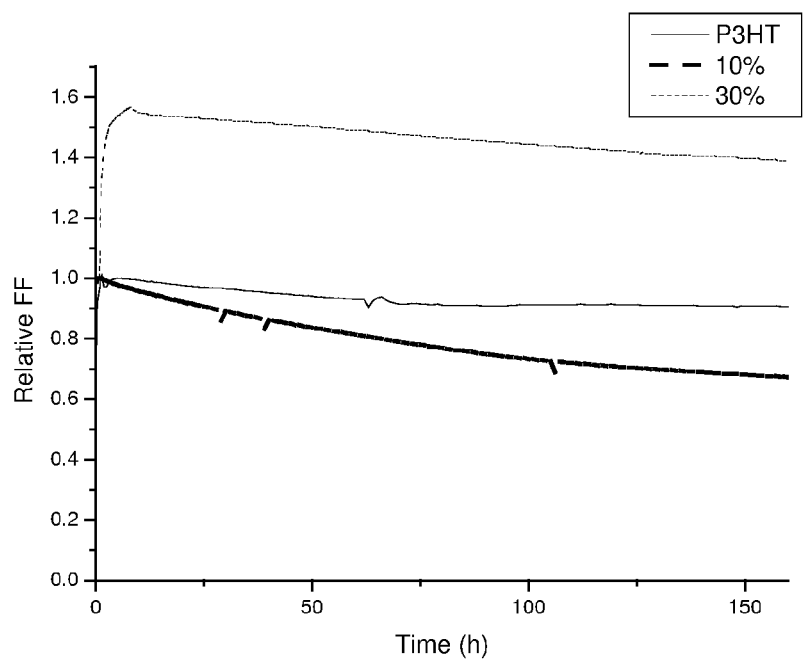
FIG. 24 is a graph of the relative Fill Factor versus time as measured on a bulk heterojunction solar cell having an active layer made from a comparative blend (Cell A) and on a bulk heterojunction solar cell having an active layer made from a P3/PCBM blend according to an embodiment of the present invention (Cell B) and on a bulk heterojunction solar cell having an active layer made from a P6/PCBM blend according to an embodiment of the present invention (Cell C) at 125° C.
Figure 25:
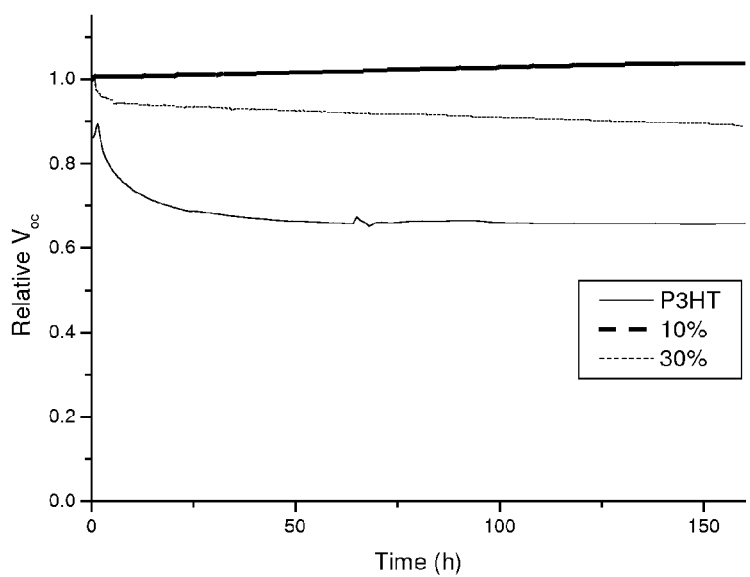
FIG. 25 is a graph of the relative open circuit voltage versus time as measured on a bulk heterojunction solar cell having an active layer made from a comparative blend (Cell A) and on a bulk heterojunction solar cell having an active layer made from a P3/PCBM blend according to an embodiment of the present invention (Cell B) and on a bulk heterojunction solar cell having an active layer made from a P6/PCBM blend according to an embodiment of the present invention (Cell C) at 125° C.
Figure 26:
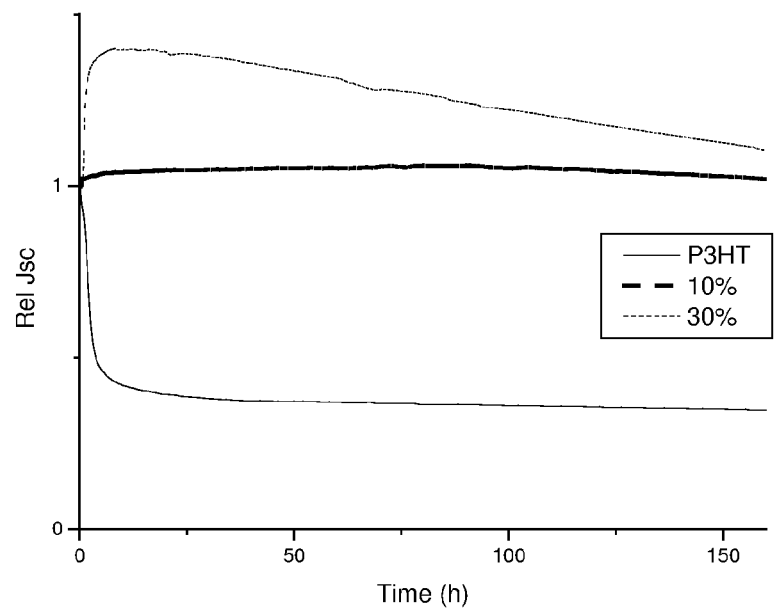
FIG. 26 is a graph of the relative short-circuit current density versus time as measured on a bulk heterojunction solar cell having an active layer made from a comparative blend (Cell A) and on a bulk heterojunction solar cell having an active layer made from a P3/PCBM blend according to an embodiment of the present invention (Cell B) and on a bulk heterojunction solar cell having an active layer made from a P6/PCBM blend according to an embodiment of the present invention (Cell C) at 125° C.
Figure 27:
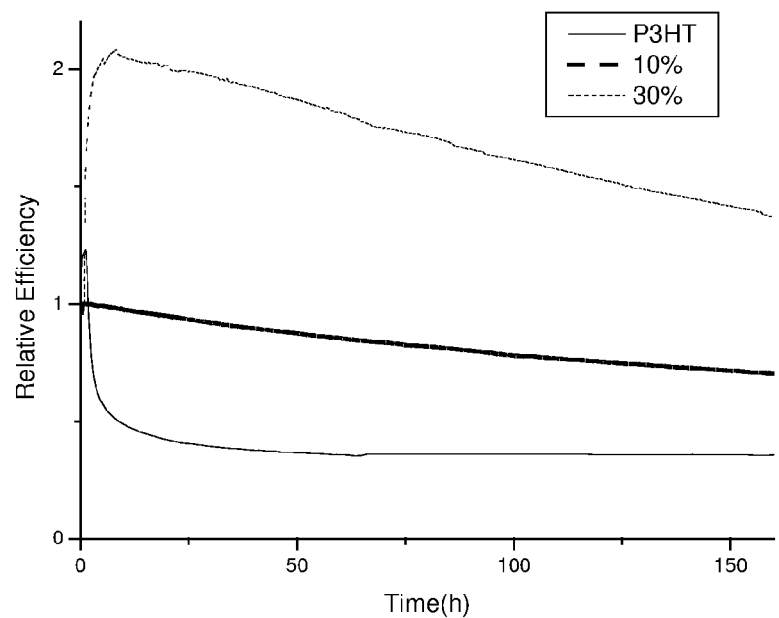
FIG. 27 is a graph of the relative power efficiency versus time as measured on a bulk heterojunction solar cell having an active layer made from a comparative blend (Cell A), on a bulk heterojunction solar cell having an active layer made from a P3/PCBM blend according to an embodiment of the present invention (Cell B) and on a bulk heterojunction solar cell having an active layer made from a P6/PCBM blend according to an embodiment of the present invention (Cell C) at 125° C.

Fabrication and Study of the Power Efficiency of Organic Bulk Heteroiunction Solar Cells Having the Random Copolymer (P3) of Example 2 as P-Type Material in the Active Layer Solar cells were prepared on glass ITO-patterned substrates. The substrates were cleaned with sonicating in soapy water, Mili-Q water, acetone and heated in isopropanol before a UV/$O_3$ treatment. A 30 nm thick PEDOT:PSS (Baytron P) layer was spincoated from aqueous dispersion on the ITO electrode. This was dried for 15 minutes at 130° C. A ca. 250 nm thick 1/1 (w/w) blend of the copolymer (P3) of example 2, containing 10% by moles of a cinnamic acid ester functionalised monomer, with PCBM active layer was spincoated from chlorobenzene solution and annealed for 10 minutes on a hotplate at 130° C. Then the Ytterbium top electrode was evaporated on the active layer in vacuum ($1.10^{-6}$ mbar) until the electrode reached a thickness of 100 nm. The active surface of each solar cell was 3 $mm^2$. After clearing the ITO contacts, I-V measurements were performed in a nitrogen atmosphere under AM 1.5G simulation, using an Oriel simulator equipped with a 150 W Xenon short arc lamp. These cells displayed a Fill Factor of 0.60. The Short Circuit Current ($J_{sc}$) reached 8.74 mA/$cm^2$. Together with an Open Circuit Voltage ($V_{oc}$) of 0.59V: this leads to a power efficiency of 3.22% comparable to a value of 3.95% with the P3HT/PCBM-blend. FIG. 11 displays the I-V curve and Table 2 compares the initial device characteristics for P3HT/PCBM- and P3/PCBM-blends.

TABLE 2

| Blend [1:1 w/w] | $J_{sc}$ [mA/$cm^2$] | $V_{OC}$ [V] | FF | Power efficiency [%] |
|---|---|---|---|---|
| P3HT/PCBM | 10.93 | 0.60 | 0.60 | 3.95 |
| P3/PCBM | 8.87 | 0.59 | 0.62 | 3.22 |

Then the cell was UV-cured for 2 hours in a nitrogen atmosphere with UV-light ($\lambda$=254 nm), whose spectrum is shown in FIG. 1, in a Lawtronics ME5 exposure unit and the power efficiency was measured again: a value of 3.22% was then measured indicating that UV curing had no influence on the power efficiency of the cell.

Example 7

Fabrication and Comparative Study of the Power Efficiency, Open Circuit Voltage, Fill Factor and Short-Circuit Current Versus Time of Two Organic Bulk Heterolunction Solar Cells Having Respectively P3HT for "Cell A" and the Random Copolymer P3 of Example 2 for "Cell B" as P-Type Material in Their Active Layer Accelerated lifetime measurements were performed on solar cells with 1:1 (w/w) blends of P3HT and the 10% cinnamic acid ester functionalized copolymer of example 2 (P3) with PCBM, after 2 hours exposure in the Lawtronics ME5 exposure unit used in Example 6 in the case of the P3/blend, and kept at temperatures of 80,100 and 150° C. in a specially developed heating chamber for at least 100 hours. The top electrode used was typically 20 nm Ca and 80 nm Al. The device was kept in the dark between measurements. The relative values for a given parameter are given as the ratio of the value at time t to the initial value at time $t_0$. In these experiments, the performances of the solar cells with P3HT/PCBM- and P3/PCBM-blends were clearly different.

The relative open circuit voltages ($V_{oc}$), Fill Factors (FF), short-circuit current ($J_{oc}$) values and power efficiencies of the solar cells with 1:1 (w/w) P3HT/PCBM-blends and P3/PCBM blends as a function of time are shown in FIG. 12 to FIG. 15 for a temperature of 80° C., FIG. 16 to FIG. 19 for a temperature of 100° C. and FIG. 20 to FIG. 23 for a temperature of 150° C. Note the different timescales at different temperatures.

At temperatures of 100° C. or less, the decline in efficiency of $J_{sc}$ proceeded according to a pseudo-linear behaviour for P3HT. This decline in efficiency was more marked than with solar cells with a crosslinked P3/PCBM active layer.

FIGS. 12 to 15 show that at a temperature of 80° C., the relative FF decreased very slightly and pseudo-linearly with time for the blend with P3, whereas the blend with P3HT exhibited slightly lower relative FF values in a pseudo-linear decrease for the first 400 hours after which the deviation in FF for the blend with P3HT increased strongly with time, the relative $V_{oc}$ values for both blends first decreased and then the relative $V_{oc}$ value for the P3-blend declined slightly linearly whereas the relative $V_{oc}$ value for the P3HT-blend first decreased slightly more strongly up to 500 hours before increasing and at 800 hours exceeded the value for the P3-blend, and the relative $V_{sc}$ value for the P3-blend first increased and then decreased pseudo-linearly passing the initial value after about 800 hours whereas the relative $J_{sc}$ value for the P3HT-blend decreased pseudo-linearly by about 20% after 800 hours. The resulting relative power efficiency values mirrored the relative $J_{sc}$-time characteristics with a reduction in relative power efficiency after 800 hours of about 7% with the P3/PCBM-blend and about 25% with the P3HT/PCBM-blend.

FIG. 16 to 19 show that at a temperature of 100° C., the relative FF value for the P3-blend initially rose slightly and then decreased linearly very slightly, whereas for the P3HT-blend there is a strong pseudo-linear decline of 12.5% after 100 hours, the relative $V_{oc}$-value for the P3-blend rose slightly and then stabilized over 100 hours whereas although the initial relative $V_{oc}$-value for the P3HT-blend was slightly higher there was a pseudo-linear decline of 15% after 100 hours, the relative short circuit current of Cell B (according to an embodiment of the present invention) was stable over time (more than 110 hours) whereas that for cell A (comparative) declined pseudo-linearly by 15% after 100 hours, and the relative power efficiency of Cell B was also stable over time (more than 110 hours) whereas that for Cell A (comparative) decreased pseudo-linearly by ca. 38% after 100 hours.

FIGS. 20 to 23 show that at a temperature of 150° C. the relative FF value decreased slightly and linearly with time for the blend with P3, whereas the blend with P3HT showed a pronounced exponential decrease in relative FF value from comparable start values, the relative $V_{oc}$-values also decreased with time with again a much reduced pseudo-linear decrease with the blend with P3 compared with a pronounced exponential decrease in the case of the blend with P3HT, and the relative $J_{sc}$ value for the blend with P3 exhibited a slight increase whereas the value for the blend with P3HT showed a pronounced exponential decrease to about 53% of the initial value after 40 hours, and the relative power efficiency for the blend with P3 increased by about 10% and then exhibited a linear back to the initial value after 50 hours whereas the power efficiency value for the blend with P3HT showed a pronounced exponential decline by about 78% of the initial value after 40 hours.

An estimate of the likely lifetime of solar cells on the basis of P3/PCBM- and P3HT/PCBM-blends at operating temperatures of 25° C. and 50° C. was made using the activation energy values derived from the data at 80, 100 and 150° C. i.e. 0.95 eV for both the P3HT/PCBM and P3/PCBM blends yielded the lifetimes to a particular decrease in short-circuit current given in Table 3 below.

TABLE 3

| Maximum permissible decrease in $J_{sc}$ | Cell A with P3HT/PCBM-blend [comparative] | | Cell B with P3/PCBM-blend [present invention] | |
| --- | --- | --- | --- | --- |
| | Lifetime at 25° C. [years] | Lifetime at 50° C. [years] | Lifetime at 25° C. [years] | Lifetime at 50° C. [years] |
| 10% | 10.9 | 0.6 | 49.3 | 2.8 |
| 20% | 21.7 | 1.2 | 98.6 | 5.6 |
| 25% | 27.1 | 1.6 | 123.2 | 7.1 |
| 50% | 54.3 | 3.1 | 246.5 | 14.1 |

The lifetime estimates are considerably longer for solar cell B with the P3/PCBM blend, according to the present invention, than for solar cell A with the P3HT/PCBM blend (comparative example) both at 25° C. and 50° C.

Example 8

Synthesis of Random Copolymers of 3-hexylthiophene (M1) and 3-(2-acetoxvethyl)thiophene (M2), Random Copolymers of 3-hexylthiophene and 3-hydroxyethylthiophene (P2), and Random Copolymers with a 7:3 Molar Ratio of 3-hexylthiophene and 3-cinnamoyloxyethylthiophene (P6)

The random copolymers with a 7:3 molar ratio of 3-hexylthiophene and 3-cinnamoyloxyethylthiophene (P6) was prepared entirely analogously to P3 except that the molar ratio of the 3-hexyl thiophene to 2,5-dibromo-3-acetylethanolthiophene (M2), 2,5-dibromo-3-ethanolthiophene (2) and cinnamoylethyl thiophene respectively was 7:3.

Example 9

Fabrication and Comparative Study of the Power Efficiency of Two Organic Bulk Heterojunction Solar Cells Having Respectively P3HT for "Cell A", the Random Copolymer P3 of Example 2 for "Cell B" as P-Type Material in Their Active Layer and the Random Copolymer P6 of Example 8 for "Cell C" as P-Type Material The solar cells of Example 9 were produced as described for Example 6 except that in addition to solar cells of with a 1:1 (w/w) P3HT/PCBM-blend and solar cells with a 1:1 (w/w) P3/PCBM-blend solar cells were also produced with a 1:1 (w/w) P6/PCBM-blend. The solar cells were kept at temperatures of 125 and 150° C. for at least 100 hours, but in the case of P3/PCBM- and P6/PCBM-blends after the solar cells were irradiated 2 hours with the UV-lamp used in Example 6. In these experiments, the performances of the solar cells made with these polymer blends were clearly different.

The relative open circuit voltages ($V_{oc}$), Fill Factors (FF), short-circuit current ($J_{sc}$) values and efficiencies of the solar cells of P3HT, P3 and P6 with PCBM (1/1) as a function of time are shown in FIG. 24 to FIG. 27 for a temperature of 125° C. The relative power efficiency with the blend of P6/PCBM-blend initially increased strongly to 200% of the initial value reflecting strong initial increases in Fill Factor and open-circuit current and even after 150 hours was still ca. 50% above its initial value, whereas the relative power efficiency in the case of the P3/PCBM-blend exhibited a pseudo-linear decline to about 75% of its initial value.

The invention claimed is:

1. A solar cell comprising:
   a substrate; and
   a stable active layer atop the substrate, the stable active layer comprising a crosslinked conjugated polymer material, obtained by irradiating a blend in an absence of a photoinitiator, said blend comprising:
   a conjugated polymer, and
   an n-type or p-type compound,
   said conjugated polymer containing one or more repeating units represented by the structural formula:

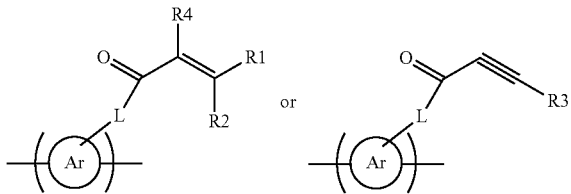

wherein:
Ar is a homocyclic or heterocyclic aromatic group selected from the group consisting of thienyl, phenyl, naphthyl, pyrrolyl, pyridyl, carbazolyl, fluorenyl and benzothiazolyl;
L is selected from the group consisting of —O—, —CH(CH$_3$)—O—, —(CH$_2$)$_q$—O—, —NH—, —CH(CH$_3$)—NH—, —(CH$_2$)$_q$—NH—, —S—, —CH(CH$_3$)—S— and —(CH$_2$)$_q$—S—, wherein the oxygen atom of said —CH(CH$_3$)—O— or —(CH$_2$)$_q$—O— is adjacent to the carbonyl group of the repeating unit, wherein the NH group of said —CH(CH$_3$)—NH— or —(CH$_2$)$_q$—NH— is adjacent to the carbonyl group of the repeating unit and, wherein the sulphur atom of said —CH(CH$_3$)—S— or —(CH$_2$)$_q$—S— is adjacent to the carbonyl group of the repeating unit;
q is 1, 2 or 3;
$R_1$ and $R_2$ are independently selected from the group consisting of hydrogen, $C_{1-4}$ alkyl and phenyl, wherein said phenyl is unsubstituted or substituted with one or more substituents independently selected from the group consisting of halogen and methoxy;
$R_3$ is selected from the group consisting of hydrogen, $C_{1-4}$-alkyl and phenyl; and
$R_4$ is hydrogen or methyl.

2. The solar cell according to claim 1, wherein said conjugated polymer further comprises one or more monomeric groups or repeating units comprising a divalent Ar', wherein Ar' is unsubstituted or substituted with one or more substituents independently selected from the group consisting of $C_{1-20}$-alkyl, $C_{1-20}$-alkoxy, $C_{1-20}$-alkylsulfate, phenyl and benzyl.

3. The solar cell according to claim 2, wherein Ar' is arylene or heteroarylene.

4. The solar cell according to claim 2, wherein Ar' and Ar are the same.

5. The solar cell according to claim 4, wherein Ar and Ar' are both 2,5-thienylene.

6. The solar cell according to claim 2, wherein Ar' represents from 0.5% to 99.5% by mole of said polymer.

7. The solar cell according to claim 2, further comprising a top electrode atop the stable active layer.

8. The solar cell according to claim 7, wherein the top electrode is a ytterbium top electrode.

9. The solar cell according to claim 2, wherein the substrate is an indium-tin oxide patterned substrate.

10. The solar cell according to claim 2, wherein the irradiating is UV irradiating, and wherein the UV irradiating does not negatively influence a power efficiency of the solar cell.

11. The solar cell according to claim 2, wherein the stable active layer further comprises a semiconducting material having an opposite type conductivity from the crosslinked conjugated polymer material.

12. The solar cell according to claim 11, wherein the semiconducting material having the opposite type conductivity from the crosslinked conjugated polymer material is a C60 derivative.

13. The solar cell according to claim 2, wherein the solar cell is an organic bulk heterojunction solar cell.

14. The solar cell according to claim 2, wherein a nanomorphology of the stable active layer is configured not to change over time at room temperature under an inert atmosphere.

* * * * *

UNITED STATES PATENT AND TRADEMARK OFFICE
CERTIFICATE OF CORRECTION

PATENT NO. : 8,450,604 B2  Page 1 of 1
APPLICATION NO. : 13/001603
DATED : May 28, 2013
INVENTOR(S) : Lutsen et al.

It is certified that error appears in the above-identified patent and that said Letters Patent is hereby corrected as shown below:

In the Specification

In column 8 at line 24, Change "tea-butylsulfate" to --tert-butylsulfate--.

In column 16 at line 40, Change "Hexylthionphene" to --Hexylthiophene--.

In column 17 at line 19, Change "$^{13}$H" to --$^{13}$C--.

In column 20 at line 62, Change "(2H$_{arom,AcET}$," to --(2H$_{a,AcET}$,--.

In column 22 at line 13 (approx.), Change "($^{2}$H$_{e,cin}$," to --(2H$_{e,cin}$,--.

In column 22 at line 15 (approx.), Change "($^{2}$H$_{a,cin}$," to --(2H$_{a,cin}$,--.

In column 22 at line 15 (approx.), Change "(2H$_{a,3HT}$)," to --(2H$_{a,3HT}$, t),--.

In column 26 at line 27, Change "Heteroiunction" to --Heterojunction--.

In column 27 at line 9, Change "Herolunction" to --Heterojunction--.

In column 27 at line 28, Change "(J$_{oc}$)" to --(J$_{sc}$)--.

In column 27 at line 50, Change "V$_{sc}$" to --J$_{sc}$--.

In column 28 at line 55, Change "2-acetoxvethyl" to --2-acetoxyethyl--.

In column 29 at line 2, Change "Heteroiunction" to --Heterojunction--.

Signed and Sealed this
Eighteenth Day of February, 2014

Michelle K. Lee
*Deputy Director of the United States Patent and Trademark Office*